(12) United States Patent
Bak-Boychuk et al.

(10) Patent No.: US 12,364,398 B2
(45) Date of Patent: Jul. 22, 2025

(54) ATRIAL STRETCH MEASUREMENT FOR ATRIAL FIBRILLATION PREVENTION

(71) Applicant: Edwards Lifesciences Corporation, Irvine, CA (US)

(72) Inventors: Gregory Bak-Boychuk, San Clemente, CA (US); Stanton J. Rowe, Newport Coast, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/066,944

(22) Filed: Dec. 15, 2022

(65) Prior Publication Data
US 2023/0119442 A1 Apr. 20, 2023

Related U.S. Application Data

(62) Division of application No. 16/179,669, filed on Nov. 2, 2018, now Pat. No. 11,529,058.

(Continued)

(51) Int. Cl.
*A61B 5/02* (2006.01)
*A61B 5/00* (2006.01)
(Continued)

(52) U.S. Cl.
CPC .......... *A61B 5/02028* (2013.01); *A61B 5/021* (2013.01); *A61B 5/062* (2013.01); *A61B 5/063* (2013.01); *A61B 5/07* (2013.01); *A61B 5/076* (2013.01); *A61B 5/1107* (2013.01); *A61B 5/1114* (2013.01); *A61B 5/1127* (2013.01); *A61B 5/6869* (2013.01); *A61B 5/6883* (2013.01); *A61B 90/39* (2016.02); *A61B 90/98* (2016.02); *A61B 5/746* (2013.01); *A61B 2017/00119* (2013.01); *A61B 2034/2051* (2016.02); *A61B 2034/2072* (2016.02);
(Continued)

(58) Field of Classification Search
None
See application file for complete search history.

(56) References Cited

U.S. PATENT DOCUMENTS 6,078,835 A * 6/2000 Hedberg ............ A61N 1/36564
607/9
6,110,100 A * 8/2000 Talpade .............. A61M 60/515
600/374

(Continued)

FOREIGN PATENT DOCUMENTS

WO WO-2014160832 A2 * 10/2014 ......... A61B 18/1492

OTHER PUBLICATIONS

Aranki et al., "Predictors of Atrail Fibrillation after Coronary Artery Bypass Surgery," Circulation, 1996, 94:390-397.

(Continued)

*Primary Examiner* — Puya Agahi
*Assistant Examiner* — Jairo H Portillo
(74) *Attorney, Agent, or Firm* — Chang & Hale LLP

(57) ABSTRACT

A stretch-measurement probe includes an elongate outer sleeve, expansion feature associated with a distal portion of the outer sleeve, and an elongate inner rod disposed at least partially within the outer sleeve. The expansion feature is configured to allow a longitudinal distance between a proximal end of the outer sleeve and the distal end of the outer sleeve to be varied.

16 Claims, 14 Drawing Sheets

Related U.S. Application Data

(60) Provisional application No. 62/591,873, filed on Nov. 29, 2017.

(51) Int. Cl.

| | | |
|---|---|---|
| *A61B 5/021* | (2006.01) | |
| *A61B 5/06* | (2006.01) | |
| *A61B 5/07* | (2006.01) | |
| *A61B 5/11* | (2006.01) | |
| *A61B 90/00* | (2016.01) | |
| *A61B 90/98* | (2016.01) | |
| *A61B 17/00* | (2006.01) | |
| *A61B 34/00* | (2016.01) | |
| *A61B 34/20* | (2016.01) | |
| *A61B 90/30* | (2016.01) | |

(52) U.S. Cl.
CPC ......... *A61B 34/25* (2016.02); *A61B 2090/061* (2016.02); *A61B 2090/064* (2016.02); *A61B 2090/309* (2016.02); *A61B 2090/372* (2016.02); *A61B 2090/3954* (2016.02); *A61B 2090/3975* (2016.02); *A61B 2090/3991* (2016.02); *A61B 2562/0223* (2013.01); *A61B 2562/0261* (2013.01); *A61B 2562/08* (2013.01)

(56) References Cited

U.S. PATENT DOCUMENTS

| | | | | |
|---|---|---|---|---|
| 7,338,436 | B1* | 3/2008 | Snell | A61F 2/2481 |
| | | | | 600/16 |
| 7,856,260 | B1* | 12/2010 | Ryu | A61N 1/0587 |
| | | | | 600/374 |
| 8,060,214 | B2* | 11/2011 | Larson | A61N 1/37223 |
| | | | | 607/60 |
| 8,278,941 | B2 | 10/2012 | Kroh et al. | |
| 2002/0147416 | A1* | 10/2002 | Zogbi | A61B 5/0031 |
| | | | | 128/899 |
| 2003/0236466 | A1* | 12/2003 | Tarjan | A61B 5/28 |
| | | | | 600/508 |
| 2004/0049105 | A1* | 3/2004 | Crutchfield | G16H 50/20 |
| | | | | 600/407 |
| 2008/0132800 | A1 | 6/2008 | Hettrick et al. | |
| 2008/0234607 | A1* | 9/2008 | Hunter-Jones | A61B 5/0055 |
| | | | | 600/587 |
| 2008/0269573 | A1* | 10/2008 | Najafi | A61B 5/6882 |
| | | | | 600/301 |
| 2010/0262029 | A1* | 10/2010 | Kelly | A61B 5/361 |
| | | | | 600/518 |
| 2012/0209345 | A1* | 8/2012 | Shkurovich | G16H 20/30 |
| | | | | 607/23 |
| 2013/0150685 | A1 | 6/2013 | Toth | |
| 2014/0180353 | A1* | 6/2014 | Mika | A61N 1/36585 |
| | | | | 607/17 |
| 2017/0035991 | A1 | 2/2017 | Rankin et al. | |
| 2017/0055909 | A1 | 3/2017 | Schibli et al. | |
| 2017/0095315 | A1 | 4/2017 | van der Weide et al. | |
| 2017/0189103 | A1 | 7/2017 | Beeckler et al. | |
| 2018/0177616 | A1* | 6/2018 | Wang | A61F 2/70 |

OTHER PUBLICATIONS

Cox, et al, "The surgical treatment of atrial fibrillation. II. Intraoperative electrophysiologic mapping and description of the electrophysiologic basis of atrial flutter and atrial fibrillation," J Thorac Cardiovasc Surg. Mar. 1991;101(3):406-26.

Echahidi, Najmeddine et. al. Mechanisms, Prevention, and Treatment of Atrial Fibrillation after Cardiac Surgery. JACC, 14. vol. 51, No. 8, 2008.

Fornengo, et al., "Prediction of atrial fibrillation recurrence after cardioversion in patients with left-atrial dilation," Eur Heart J Cardiovasc Imaging. Mar. 2015;16(3):335-41.

Hatam, et al., "Interatrial conduction disturbance in postoperative atrial fibrillation: a comparative study of P-wave dispersion and Doppler myocardial imaging in cardiac surgery," J Cardiothorac Surg. Jun. 24, 2014;9:114. doi: 10.1186/1749-8090-9-114.

Jorge, et al., "Early detection of acute transmural myocardial ischemia by the phasic systolic-diastolic changes of local tissue electrical impedance," Integrative Cardiovascular Physiology and Pathophysiology, Feb. 1, 2016 https://doi.org/10.1152/ajpheart.00754.2015.

Kardon, Merrill, "A Simple Portable Sonomicrometer", Nov. 1966, USAF School of Aerospace Medicine, Aerospace Medical Division (AFSC), Brooks Air Force Base, Texas.

Klaus, et al., "Assessment of fluid balance by measurement of skin tissue thickness during clinical anaesthesia," Clin Physiol Funct Imaging. May 2002;22(3):197-201.

Lazzeroni, et al., "P-wave dispersion predicts atrial fibrillation following cardiac surgery," Int J Cardiol. Jan. 15, 2016;203:131-3. doi: 10.1016/j.ijcard.2015.10.143. Epub Oct. 19, 2015.

Lee, et al, "Left atrial volume index as a predictor for occurrence of atrial fibrillation after ablation of typical atrial flutter," J Cardiol. Nov. 2010;56(3):348-53.

Mathew, Joseph et al., "A Multicenter Risk Index for Atrial Fibrillation after Cardiac Surgery," JAMA, Apr. 14, 2004 v. 291.

Teixeira, et al., "Left atrial appendage volume as a new predictor of atrial fibrillation recurrence after catheter ablation," J Interv Card Electrophysiol. Aug. 2017;49(2):165-171.

Uijl, et al., "Left Atrial Size as a Predictor of Successful Radiofrequency Catheter Ablation for Atrial Fibrillation," Europace, 2009, 11 (10), 1255-1256, Oct. 1, 2009.

Zhang Tianshuo et al, "A Wireless smartphone-aided magnetic strain sensor for biomedical applications", 2017 IEEE 30th International conference on Micro Electro Mechanical Systems (MEMS), IEEE, Jan. 22, 2017 (Jan. 22, 2017), pp. 235-238 XP033069501, DOI: 10.1109/MEMSYS.2017.7863384 [retrieved on Feb. 23, 2017] the whole document.

* cited by examiner

ATRIAL STRETCH MEASUREMENT FOR ATRIAL FIBRILLATION PREVENTION

RELATED APPLICATION

This application claims priority to U.S. application Ser. No. 16/179,669, filed on Nov. 2, 2018 and U.S. Provisional Application No. 62/591,873, filed Nov. 29, 2017, and entitled ATRIAL STRETCH MEASUREMENT FOR ATRIAL FIBRILLATION PREVENTION, the disclosures of which are hereby incorporated by reference in their entireties.

BACKGROUND

The present disclosure generally relates to the field of medical surgery, such as cardiac surgery. Patients of cardiac surgery and other vascular operations can develop complications associated with fluid overload and/or atrial fibrillation post-operatively due to various conditions and/or factors. Atrial fibrillation is associated with certain health complications, including increased patient mortality, and therefore prevention and/or treatment of atrial fibrillation during surgery and/or post-operatively can improve patient health.

SUMMARY

In some implementations, the present disclosure relates to a stretch-measurement probe comprising an elongate outer sleeve, an expansion feature associated with a distal portion of the outer sleeve, and an elongate inner rod disposed at least partially within the outer sleeve. The expansion feature is configured to allow a longitudinal distance between a proximal end of the outer sleeve and a distal end of the outer sleeve to be varied.

The expansion feature may comprise a flexible spring. In certain embodiments, the expansion feature and the outer sleeve are a unitary form. The expansion feature may be formed at least in part by a cut in the outer sleeve. In certain embodiments, the outer sleeve is at least partially transparent. In certain embodiments, the proximal end of the outer sleeve comprises one or more stretch indicator markings. Additionally or alternatively, a proximal end of the inner rod may comprise one or more stretch indicator markings. In certain embodiments, the inner rod is fixed to the outer sleeve at an attachment point of the outer sleeve. For example, the expansion feature may be positioned between the attachment point of the outer sleeve and a distal end of the outer sleeve.

The stretch-measurement probe may further comprise a first sensor element associated with a distal end of the outer sleeve, and a second sensor element associated with a distal end of the inner rod. For example, one of the first and second sensor elements may comprise a magnet, and the other of the first and second sensor elements may comprise a Hall effect sensor. One or more of the first and second sensor elements may be configured to provide a voltage signal indicating a distance between the first and second sensor elements.

In certain embodiments, the stretch-measurement probe further comprises a pull-release wire disposed at least partially within the outer sleeve and between the outer sleeve and the inner rod. For example, the pull-release wire may be coupled to a handle at a proximal end of the pull-release wire.

In some implementations, the present disclosure relates to an implantable device for monitoring atrial stretch. The method comprises electrically-conductive material configured to be sensed by a monitor device through a chest wall and means for securing the implantable device to a surface of an atrium of a heart.

The implantable device may further comprise a magnet. In certain embodiments, the implantable device further comprises a biocompatible housing, a radio-frequency identification (RFID) circuitry disposed within the housing, an antenna, and non-volatile data storage configured to store identification information associated with the implantable device, wherein the RFID circuitry is configured to facilitate transmission of the identification information wirelessly through the chest wall. The electrically-conductive material may comprise a conductive coil. In certain embodiments, the implantable device further comprises a sensor element configured to sense one or more other implantable devices disposed in proximity thereto.

In some implementations, the present disclosure relates to a method of monitoring stretching of an organ. The method comprises suturing an outer sleeve of a stretch-measurement probe to a surface of an atrium of a heart of a patient at a first attachment point of the outer sleeve, the stretch-measurement probe comprising an inner rod disposed at least partially within the outer sleeve. The method further comprises suturing the outer sleeve to the surface of the atrium at a second attachment point of the outer sleeve, the second attachment point being longitudinally spaced from the first attachment point by a first distance. The method further comprises disposing the stretch-measurement probe in a chest access channel in a chest of the patient, and, when the surface of the atrium has stretched, thereby causing an expansion feature of the stretch-measurement probed to expand between the first and second attachment points such that the second attachment point becomes longitudinally spaced from the first attachment point by a second distance that is greater than the first distance, determining an amount of stretch associated with surface of the atrium based at least in part on a relative movement of a proximal portion of the outer sleeve with respect to a proximal portion of the inner rod.

The method may further comprise closing a chest cavity of the patient prior to determining the amount of stretch. Suturing the outer sleeve to the surface of the atrium at the first attachment point may comprise passing a suture through an opening in the expansion feature and around a wire disposed at least partially within the outer sleeve. In certain embodiments, the method further comprises removing the stretch-measurement probe from the chest of the patient through the chest access channel while the chest of the patient is substantially closed. The method may further comprise pulling a pull-release wire disposed at least partially within the outer sleeve prior to said removing the stretch-measurement probe. Removing the stretch-measurement probe may comprise pulling the stretch-measurement probe through the chest access channel.

In some implementations, the present disclosure relates to a method of monitoring stretching of an organ. The method comprises implanting a plurality of electrically-conductive markers on a surface of an atrium of a heart of a patient, closing a chest cavity of the patient, approximating a monitor device to a chest of the patient, detecting the plurality of electrically-conductive markers using the monitor device, and determining location information associated with the plurality of electrically-conductive markers using the monitor device.

The plurality of electrically-conductive markers may comprise three electrically-conductive markers. In certain embodiments, implanting the plurality of electrically-conductive markers comprises suturing the plurality of electrically-conductive markers to the surface of the atrium. The method may further comprise adhering the monitor device to the chest of the patient.

In some implementations, the present disclosure relates to an atrial stretch monitoring system comprising a plurality of electrically-conductive markers configured to be implanted on a surface of an atrium of a heart, and a monitor device configured to detect locations of the plurality of electrically-conductive markers through a chest wall when the electrically-conductive markers are implanted on the surface of the atrium.

In some implementations, the present disclosure relates to a method of determining an atrial stretch limit. The method comprises determining first location information associated with a plurality of electrically-conductive marker devices implanted on a surface of an atrium of a heart of a patient, administering a fluid bolus to the patient, determining second location information associated with the plurality of electrically-conductive marker devices after said administering the fluid bolus, and setting an alarm setpoint based on the second location information. In certain embodiments, the method further comprises recording a baseline vascular pressure level prior to administering the fluid bolus and recording a post-bolus vascular pressure level after administering the fluid bolus.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

DETAILED DESCRIPTION

Figure 1:
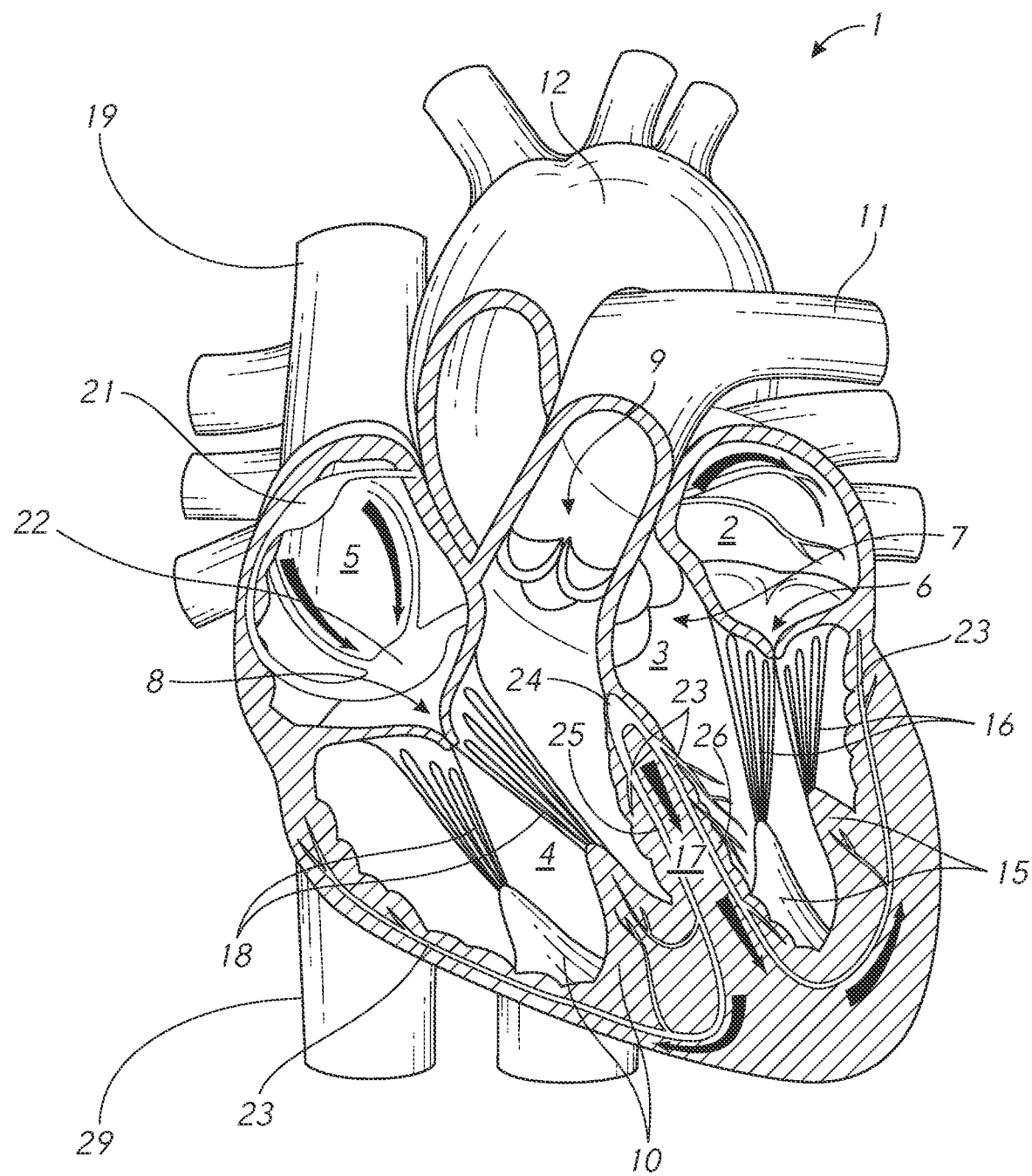
FIG. 1 provides an example cross-sectional view of a human heart.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Furthermore, references may be made herein to certain anatomical planes, such as the sagittal plane, or median plane, or longitudinal plane, referring to a plane parallel to the sagittal suture, and/or other sagittal planes (i.e., para-sagittal planes) parallel thereto. In addition, "frontal plane," or "coronal plane," may refer to an X-Y plane that is perpendicular to the ground when standing, which divides the body into back and front, or posterior and anterior, portions. Furthermore, a "transverse plane," or "cross-sectional plane," or horizontal plane, may refer to an X-Z plane that is parallel to the ground when standing, that divides the body in upper and lower portions, such as superior and inferior. A "longitudinal plane" may refer to any plane perpendicular to the transverse plane. Furthermore, various axes may be described, such as a longitudinal axis, which may refer to an axis that is directed towards head of a human in the cranial direction and/or directed towards inferior of a human in caudal direction. A left-right or horizontal axis, which may refer to an axis that is directed towards the left-hand side and/or right-hand side of a patient. An antero-posterior axis which may refer to an axis that is directed towards the belly of a human in the anterior direction and/or directed towards the back of a human in the posterior direction.

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.). The contraction of the various heart muscles may be prompted by signals generated by the electrical system of the heart, which is discussed in detail below. Certain embodiments disclosed herein relate to conditions of the heart, such as atrial fibrillation and/or complications or solutions associated therewith. However, embodiments of the present disclosure relate more generally to any health complications relating to fluid overload in a patient, such as may result post-operatively after any surgery involving fluid supplementation. That is, detection of atrial stretching as described herein may be implemented to detect/determine a fluid-overload condition, which may direct treatment or compensatory action relating to atrial fibrillation and/or any other condition caused at least in part by fluid overloading.

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11 and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size and position of the leaflets or cusps may be such that when the heart contracts, the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage.

The atrioventricular (i.e., mitral and tricuspid) heart valves may further comprise a collection of chordae tendineae (16, 18) and papillary muscles (10, 15) for securing the leaflets of the respective valves to promote and/or facilitate proper coaptation of the valve leaflets and prevent prolapse thereof. The papillary muscles (10, 15), for example, may generally comprise finger-like projections from the ventricle wall. With respect to the mitral valve 6, a normal mitral valve may comprise two leaflets (anterior and posterior) and two corresponding papillary muscles 15. When the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles by the chordae tendineae 17, which are disposed in the right ventricle 4 along with the papillary muscles 10. The right ventricular papillary muscles 10 originate in the right ventricle wall, and attach to the anterior, posterior and septal leaflets of the tricuspid valve, respectively, via the chordae tendineae 17.

Fluid overload or volume overload, which is referred to as hypervolemia, is a medical condition in which the vasculature contains too much fluid. Fluid-overload conditions can arise in connection with various types of surgical operations, including cardiac surgery. For example, fluid management through fluid infusion may be necessary or desirable in order to maintain adequate cardiac output, systemic blood pressure, and/or renal perfusion during or in connection with a surgical operation. Example settings in which fluid overload may develop include the administration of excessive fluid and sodium due to intravenous (IV) or fluids during surgical operations, such as atrial fibrillation ablation, valve repair or replacement, or other cardio/thoracic procedures, or fluid remobilization procedures associated with burn or trauma treatment.

Fluid overload can correlate with mortality in certain categories of patients. In order to restore or maintain desired fluid levels, it may be necessary or desirable to determine present volume status. According to some practices, fluid overload recognition and assessment involves strict documentation of fluid intakes and outputs. However, accuracy is fluid intake/output tracking can be difficult to achieve over time, and there are a wide variety of methods utilized to evaluate, review, and utilize fluid tracking data. Furthermore, errors in volume status determination can result in a lack of essential treatment or unnecessary fluid administration, either of which can present serious health risks.

As described herein, fluid overload associated with fluid administration of fluid in association with a surgical operation can result in post-operative onset of atrial fibrillation. Furthermore, fluid overload conditions can cause or be associated with various other conditions, including pulmonary edema, cardiac failure, delayed recovery, tissue breakdown, and/or at least partially impaired function of bowels or other organs. Therefore, the evaluation of volume status can be important before, during, and/or after a surgical operation, such as cardia surgery. Once identified, fluid overload may be treated in a variety of ways, including cessation or reduction of fluid administration, administration of diuretics, and/or fluid/letting.

For at least the reasons outlined above, determination/detection of fluid overload conditions can be critical or important to prevention or treatment of various adverse health conditions. However, the lack of available volume overload sensors that conveniently and accurately measure or indicate fluid overload can be problematic. Embodiments of the present disclosure provide improved systems, devices, and methods for determining/detecting a fluid overload condition by monitoring tissue stretching in fluid-containing organs or tissue. For example, tissue stretching in an atrium (or ventricle) of a hear, as described in detail herein, can indicate a fluid overload, or impending fluid overload, condition. The embodiments of the present disclosure advantageously provide removable devices/systems for measuring tissue stretching associated with fluid overload in a relatively convenient manner compared to pressure measurement fluid tracking using, for example, peripherally-inserted central catheter (PICC or PIC line), or other known mechanism for tracking of fluid pressure or other characteristic(s). Certain embodiments of the present disclosure provide improvements over other patient monitoring solutions by providing systems, devices, and methods for directly measuring organ or tissue stretching, wherein it is not necessary to infer tissue stretching from echo or x-ray imaging. Direct tissue-measuring in accordance with embodiments of the present disclosure may be used to measure atrial tissue stretching, or stretching of other organs or tissue, including but not limited to gestational stretch measurement of uterine tissue or other pregnancy-related stretching, prostate stretching/enlargement, liver tissue stretching, colon stretching/enlargement, or other tissue/organ.

The electrical system of the heart generally controls the events associated with the pumping of blood by the heart. With further reference to FIG. 1, the heart 1 comprises different types of cells, namely cardiac muscle cells (also known as cardiomyocytes or myocardiocytes) and cardiac pacemaker cells. For example, the atria (2, 5) and ventricles (3, 4) comprise cardiomyocytes, which are the muscle cells that make up the cardiac muscle. The cardiac muscle cells are generally configured to shorten and lengthen their fibers and provide desirable elasticity to allow for stretching. Each myocardial cell contains myofibrils, which are specialized organelles consisting of long chains of sarcomeres, the fundamental contractile units of muscle cells.

The electrical system of the heart utilizes the cardiac pacemaker cells, which are generally configured to carry electrical impulses that drive the beating of the heart 1. The cardiac pacemaker cells serve to generate and send out electrical impulses, and to transfer electrical impulses cell-to-cell along electrical conduction paths. The cardiac pacemaker cells further may also receive and respond to electrical impulses from the brain. The cells of the heart are connected by cellular bridges, which comprise relatively porous junctions called intercalated discs that form junctions between the cells. The cellular bridges permit sodium, potassium and calcium to easily diffuse from cell-to-cell, allowing for depolarization and repolarization in the myocardium such that the heart muscle can act as a single coordinated unit.

The electrical system of the heart comprises the sinoatrial (SA) node 21, which is located in the right atrium 5 of the heart 1, the atrioventricular (AV) node 22, which is located on the interatrial septum in proximity to the tricuspid valve 8, and the His-Purkinje system 23, which is located along the walls of the left 3 and right 4 ventricles.

A heartbeat represents a single cycle in which the heart's chambers relax and contract to pump blood. As described above, this cycle includes the opening and closing of the inlet and outlet valves of the right and left ventricles of the heart. Each beat of the heart is generally set in motion by an electrical signal generated and propagated by the heart's electrical system. In a normal, healthy heart, each beat begins with a signal from the SA node 21. This signal is generated as the vena cavae (19, 29) fill the right atrium 5 with blood, and spreads across the cells of the right 5 and left 2 atria. The flow of electrical signals is represented by the illustrated shaded arrows in FIG. 1. The electrical signal from the SA node 21 causes the atria to contract, which pushes blood through the open mitral 6 and tricuspid 8 valves from the atria into the left 3 and right 4 ventricles, respectively.

The electrical signal arrives at the AV node 22 near the ventricles, where it may slow for an instant to allow the right 4 and left 3 ventricles to fill with blood. The signal is then released and moves along a pathway called the bundle of His 24, which is located in the walls of the ventricles. From the bundle of His 24, the signal fibers divide into left 26 and right 25 bundle branches through the Purkinje fibers 23. These fibers connect directly to the cells in the walls of the left 3 and right 4 ventricles. The electrical signal spreads across the cells of the ventricle walls, causing both ventricles to contract. Generally, the left ventricle may contract an instant before the right ventricle. Contraction of the right ventricle 4 pushes blood through the pulmonary valve 9 to the lungs (not shown), while contraction of the left ventricle 3 pushes blood through the aortic valve 6 to the rest of the body. As the electrical signal passes, the walls of the ventricles relax and await the next signal.

FIG. 1, as described above, illustrates a normal electrical flow, resulting in a regular heart rhythm, that may be associated with a generally healthy heart. However, in certain patients or individuals, various conditions and/or events can result in compromised electrical flow, causing the development and/or occurrence of an abnormal heart rhythm. For example, atrial fibrillation is a condition associated with abnormal electrical flow and/or heart rhythm characterized by relatively rapid and irregular beating of the atria.

Figure 2:
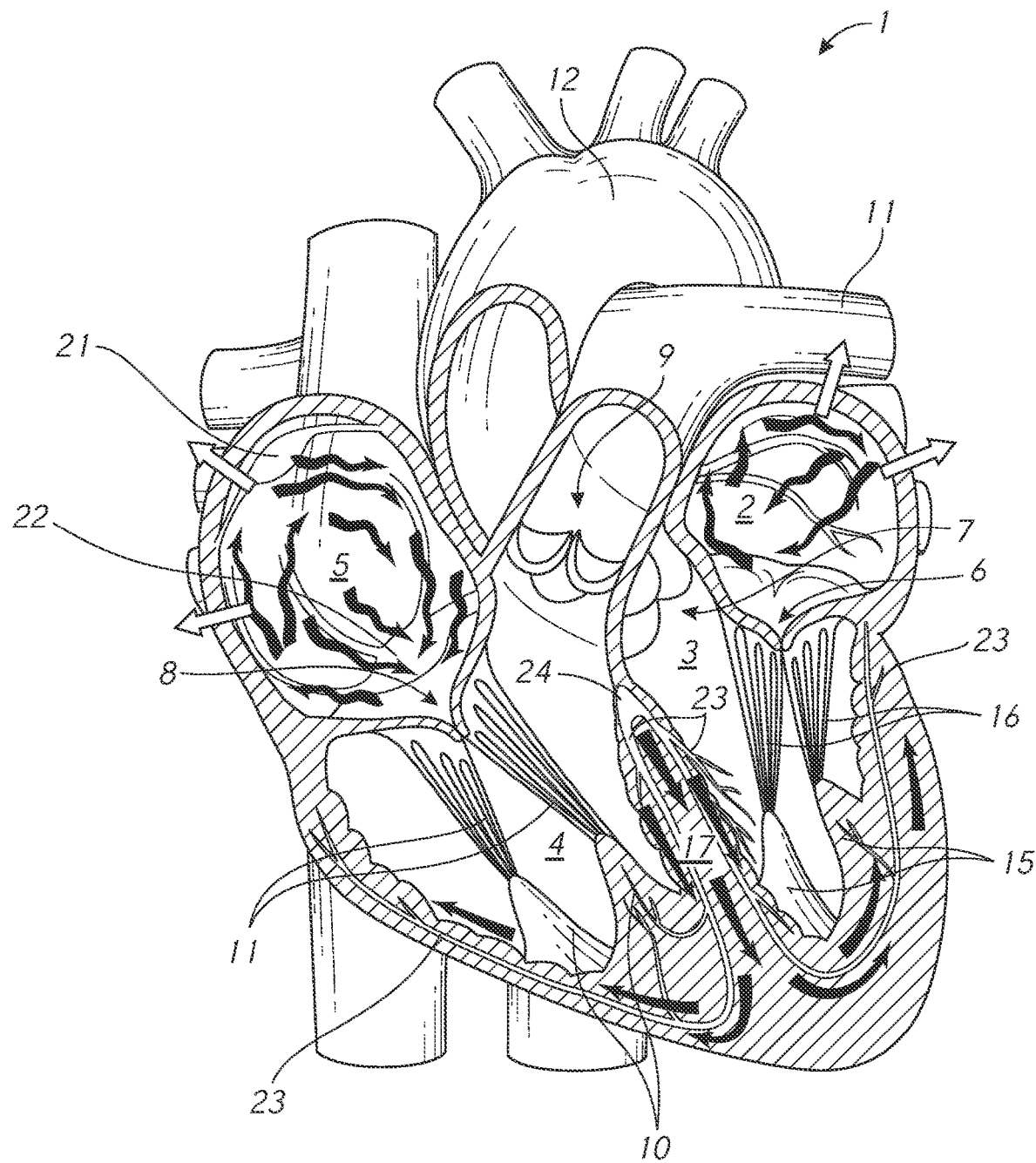
FIG. 2 illustrates an example cross-sectional representation of a heart experiencing atrial fibrillation.

FIG. 2 illustrates an example cross-sectional representation of the heart 1 of FIG. 1 experiencing atrial fibrillation. When atrial fibrillation occurs, the normal regular electrical impulses generated by the sinoatrial (SA) node 21 in the right atrium 5 may become overwhelmed by disorganized electrical impulses, which may lead to irregular conduction of ventricular impulses that generate the heartbeat. The illustrated shaded arrows represent the erratic electrical impulses that can be associated with atrial fibrillation. Atrial fibrillation generally originates in the right atrium 5, that where conduction path disturbances begin.

Various pathologic developments can lead to, or be associated with, atrial fibrillation. For example, progressive fibrosis of the atria may contribute at least in part to atrial fibrillation. The formation of fibrous tissue associated with fibrosis can disrupt or otherwise affect the electrical pathways of the cardiac electrical system due to interstitial expansion associated with tissue fibrosis. In addition to fibrosis in the muscle mass of the atria, fibrosis may also occur in the sinoatrial node 21 and/or atrioventricular node 22, which may lead to atrial fibrillation.

Fibrosis of the atria may be due to atrial dilation, or stretch, in some cases. Dilation of the atria can be due to a rise in the pressure within the heart, which may be caused by fluid overload, or may be due to a structural abnormality in the heart, such as valvular heart disease (e.g., mitral stenosis, mitral regurgitation, tricuspid regurgitation), hypertension, congestive heart failure, or other condition. Dilation of the atria can lead to the activation of the renin aldosterone angiotensin system (RAAS), and subsequent increase in matrix metalloproteinases and disintegrin, which can lead to atrial remodeling and fibrosis and/or loss of atrial muscle mass.

In addition to atrial dilation, inflammation in the heart can cause fibrosis of the atria. For example, inflammation may be due to injury associated with a cardiac surgery, such as a valve repair operation, or the like. Alternatively, inflammation may be caused by sarcoidosis, autoimmune disorders, or other condition. Other cardiovascular factors that may be associated with the development of atrial fibrillation include high blood pressure, coronary artery disease, mitral stenosis (e.g., due to rheumatic heart disease or mitral valve prolapse), mitral regurgitation, hypertrophic cardiomyopathy (HCM), pericarditis, and congenital heart disease. Additionally, lung diseases (such as pneumonia, lung cancer, pulmonary embolism, and sarcoidosis) may contribute to the development of atrial fibrillation in some patients.

In addition to the various physiological conditions described above that may contribute to atrial fibrillation, in some situations, atrial fibrillation may be developed in connection with a vascular operation, such post-operatively in the days following a vascular operation. Various factors may bear on the likelihood of a patient developing post-operative atrial fibrillation, such as age, medical history (e.g., history of atrial fibrillation, chronic obstructive pulmonary disease (COPD)), concurrent valve surgery, withdrawal of post-operative treatment (e.g., beta-adrenergic blocking agents (i.e., beta blocker), angiotensin converting enzyme inhibitors (ACE inhibitor)), beta-blocker treatment (e.g., pre-operative and/or post-operative), ACE inhibitor treatment (e.g., pre-operative and/or post-operative), and/or other factors. Generally, for patients that experience post-operative atrial fibrillation, the onset of atrial fibrillation may occur approximately 2-3 days after surgery.

Atrial dilation/stretching may be considered a primary variable associated with post-operative atrial fibrillation. In some situations, occurrence of post-operative atrial fibrillation may follow, at least in part, the following progression: First, the patient undergoes a surgical procedure, such as a vascular surgical operation (e.g., cardiac surgery). In connection with the operation, the patient may be subject to drug and/or fluid management. For example, the patient may receive post-surgery intravenous (IV) fluid loading and/or diuretic/drug volume management. Such treatment may result in fluid overload, which may lead to atrial stretching due to increased pressure in one or more atria. Atrial stretching may occur over a 1-2 day period, or longer, resulting in dilation of one or both of the atria. Fibrotic atrial tissue may form in connection with atrial stretching. Atrial stretching and/or fibrotic atrial tissue formation may result in an increased incidence of post-operative atrial fibrillation (e.g., 30-40% increased incidence of post-operative atrial fibrillation). In addition, inflammation associated with surgical operations can contribute the onset of post-operative atrial fibrillation, and reduced inflammation may generally correlate to a reduced risk of atrial fibrillation.

Post-operative atrial fibrillation is generally associated with increased patient morbidity, as well as economic burden. For example, post-operative atrial fibrillation is generally associated with increased incidence of congestive heart failure, increased hemodynamic instability, increase renal insufficiency, increased repeat hospitalizations, increased risk of stroke, and increase in hospital mortality and 6-month mortality. Post-operative atrial fibrillation also represents a systemic burden, wherein intensive care unit (ICU) stay, hospital length of stay, hospital charges, and rates of discharge to extended care facilities are increased as a result of post-operative atrial fibrillation.

Furthermore, because an initial incidence of atrial fibrillation generally results in recurring, progressively more severe, episodes of atrial fibrillation in a patient, the consequences of allowing atrial fibrillation to develop post-operatively can be considered particularly severe for a given patient. For example, a given patient may initially experience intermittent/sporadic episodes of atrial fibrillation as a result of post-operative atrial dilation and/or inflammation, with recurring episodes progressively increasing in frequency and/or severity.

As discussed above, stretching, and in particular prolonged stretching, of atrial tissue can result in intracellular tissue damage, which may at least partially disturbed natural electrical conduction paths for the electrical conduction system of the heart, particularly with respect to relatively older patients and/or patients suffering from one or more other physiological conditions. Therefore, measurement of atrial stretch, which in turn can be used to direct prevention efforts, can help reduce incidences of atrial fibrillation. Embodiments of devices and processes disclosed herein may provide mechanisms for measuring the amount of atrial stretch experienced by a patient, and in particular, mechanisms for measuring atrial stretch post-operatively, such as when the chest cavity of the patient may be closed and not directly accessible. Although atrial stretching is described in detail in connection with certain embodiments disclosed herein, it should be understood that such embodiments may be applicable to tissue-stretching detection/measurement with respect to other types of organs or tissue, or even to other types of materials in non-biological applications.

Certain embodiments disclosed herein provide systems, devices, and/or methods for monitoring the amount or degree of stretching experienced by one or more atria of a heart. Information relating to the amount of atrial stretch experienced by a patient may be relied upon and/or used in connection with fluid management of the patient. For example, where atrial stretch beyond a certain amount is detected or predicted, intravenous (IV) fluid infusion for the patient may be adjusted in accordance therewith.

The development of atrial fibrillation post-operatively can have a serious negative impact on patient quality of life. The majority of post-operative atrial fibrillation instances may occur within the first two days after surgery, and therefore, prevention of post-operative atrial stretch and/or inflammation may be particularly significant during the initial days after surgery. Generally, atrial diameter expansion of greater than 4-5 mm may be correlated with chronic atrial fibrillation in some cases. Furthermore, increase in atrial circumference of greater than 10%, and/or increase in atrial volume of greater than 8.5 mL may be associated with chronic atrial fibrillation. Certain embodiments disclosed herein facilitate the measurement of atrial stretch within the days following a surgical operation, and further may provide resolution of measurement of atrial stretch of that is adequate for measuring 5 mm of circumferential stretch or less, or 10% or less of circumferential stretch.

Various devices and/or mechanisms may be implemented to provide atrial stretch measurement. For example, certain embodiments disclosed herein provide removable measurement devices configured to provide direct measurement of atrial stretch, and/or other conditions of the heart. In some embodiments, atrial stretch measurement is implemented using implantable devices that may comprise one or more sensors for measuring atrial stretch. For example, such implantable devices may implement impedance-based and/or magnetic sensor technology for determining the location, or relative location, of the implanted device(s). In some embodiments, atrial stretch measurement devices comprise metal and/or magnetic button/tack-type implantable devices, as described in detail below.

Removable direct atrial stretch measurement devices in accordance with the present disclosure may comprise, in certain embodiments, strain-gauge-type devices, or the like. For example, an atrial stretch measurement device may comprise a strain gauge configured to experience strain corresponding to stretch in one or more atria of the heart. With respect to strain-gauge-type embodiments, such devices may advantageously provide sufficient flexibility to accommodate the biology, pressure, and/or degree of stretch typically associated with the atria of the heart. Strain-gauge-based atrial measurement devices in accordance with the present disclosure may comprise electronic strain gauge devices configured to measure and/or provide information indicating measured resistance/impedance, wherein such resistance/impedance may vary in correspondence with the amount of force and/or strain applied thereto or experienced thereby. Although certain atrial stretch devices/probes in accordance with the present disclosure may comprise resistance/impedance-based strain gauge measurement, any other type of strain-measuring devices/probes may be used in accordance with the embodiments of the present disclosure.

As described in detail below in connection with FIGS. 3-9, atrial stretch measurement devices may comprise directly-implantable sensor marker devices configured to provide relative distance measurement functionality. In some embodiments, such devices may comprise magnetic sensor devices, such as Hall effect sensors, or the like.

Figure 3:
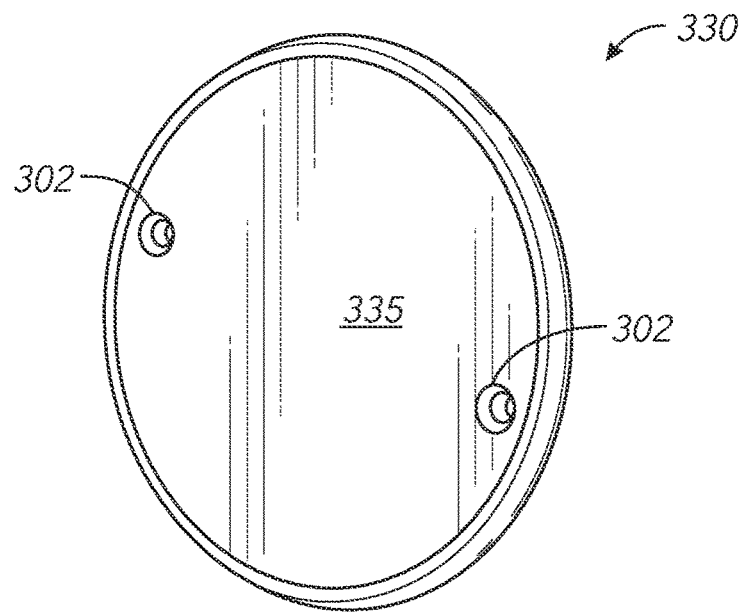
FIG. 3 illustrates a perspective view of an implantable stretch detection marker device in accordance with one or more embodiments.

FIG. 3 illustrates a perspective view of an implantable stretch detection marker device 330 in accordance with one or more embodiments of the present disclosure. The term "marker" is used herein according to its broad and ordinary meaning and may refer to any device that may be configured to provide information associated a physiological area or environment associated therewith. For example, atrial stretch detection markers, as described herein, may comprise relatively small implantable devices that may be used to generate or provide information relating physical position and/or to atrial stretch associated with a heart or atrium on which the marker is disposed or implanted.

The marker device 330 may be implanted in a patient in connection with a surgical operation. For example, a physician may have access to the heart of a patient during a thoracic surgery, in which the chest cavity of the patient may be at least partially open. While the chest cavity is open, the physician may suture or otherwise implant a plurality of atrial stretch marker devices, such as devices like the marker device 330 shown in FIG. 3. Such atrial stretch measurement/detection devices may be implanted in groups of two, three, or other number of marker devices. In some embodiments, a marker device implanted on the patient's heart may comprise a magnet, which may be dimensioned and/or positioned to be sensed by a sensing device external to the chest when the chest cavity is closed.

In some embodiments, the stretch-detection marker device 330 incorporates radio-frequency identification (RFID) functionality, which may allow for certain data to be retrieved from, or provided by, the implanted marker(s) after implantation thereof. For example, the marker device 330 may comprise circuitry for storing and processing information, as well as an antenna to receive and transmit a signal from an external reader device. The marker device 330 may include non-volatile memory storage, wherein data stored there may be provided to an external reader device in response to interrogation by the external reader device. The marker device 330 may be configured to convert a radio signal received from the reader device into usable power for responding to the reader.

In some embodiments, the marker device 330 may comprise a conductive coil (not shown). For example, the inductive coil may be wrapped at least partially around an iron/ferrite core in some implementations. The coil may be inductively sensed by a sensor device, wherein such sensing may indicate physical positioning of the marker device 330 and/or other information associated with atrial stretch. In some embodiments, the marker device 330 is charged with electromotive force (EMF), such that the device 330 may be sensed using radio telemetry technology. In certain embodiments, the marker device 330 may be constructed of, or comprise, biocompatible materials, which may advantageously be implanted on the atria tissue without causing irritation to surrounding in contact or proximity therewith.

The marker device 330 may comprise one or more holes or apertures 302, which may be used for suturing or otherwise affixing the marker device 330 to the surface of the atrium. The top or outer surface 335 of the marker device 330 may comprise a substantially smooth surface. In certain embodiments, the exterior of the marker device 330 may provide a housing for internal electronics. Such electronics may advantageously be protected from fluid and/or other environmental conditions associated with the implant environment. In some embodiments, the housing of the marker device 330 may comprise plastic or other material.

Marker devices in accordance with the present disclosure may comprise certain additional features or characteristics. For example, a marker device like the device 330 shown in FIG. 3 may store or comprise data or other identifier(s) that may indicate identification information associated with the marker device 330. For example, patient data, date of implantation, relative position of the marker relative to other implanted markers, or other information may be stored and/or recorded in or on the marker device 330. Such information may be accessible in any suitable or desirable way, such as through radio-frequency identification (RFID) technology, as referenced above, or the like. In some implementations, the marker device 330 may be configured to use radio telemetry to communicate with another marker device implanted on the heart.

Figure 4:
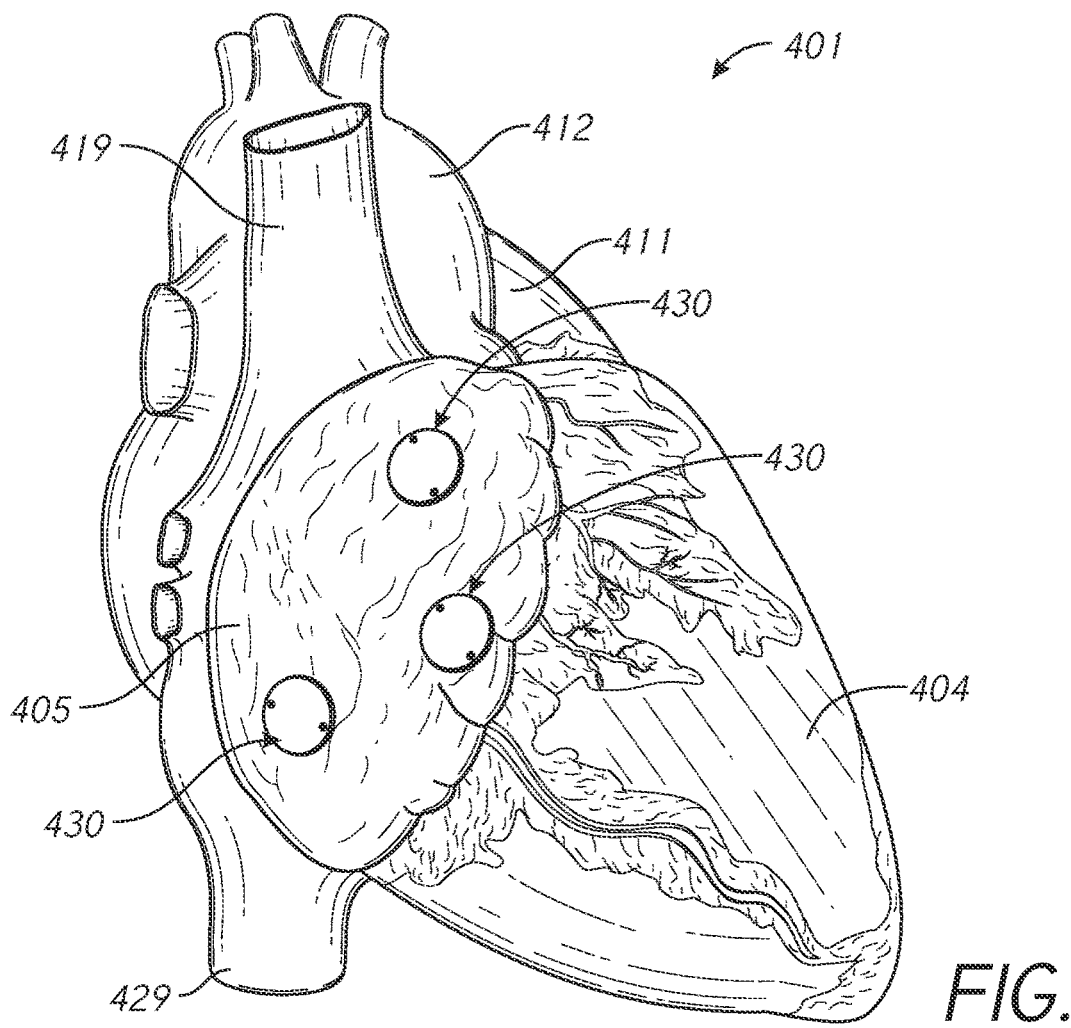
FIG. 4 illustrates a perspective view of a heart having one or more marker devices implanted on an atrium thereof in accordance with one or more embodiments.

FIG. 4 illustrates a perspective view of a heart 401 having one or more marker devices 430 implanted on one or more atria thereof (e.g., right atrium 105). In some implementations, a plurality of marker devices 430, such as three marker devices, as shown, are surgically affixed in some manner to the surface of the right atrium 105, and/or left atrium (not shown). The marker devices 430 may be affixed to the surface of the atrium 105 in any suitable or desirable manner, such as through the use of suturing, adhesive substance, or other means of physically fixing and/or securing the devices 430 to the atrium surface.

As referenced above, after the stretch measurement/detection marker devices 430 have been implanted on the atrium surface, the chest cavity of the patient may be closed, such that direct access to the devices is inhibited or unfeasible. However, embodiments disclosed herein provide systems and devices for externally communicating with, or otherwise monitoring or detecting, the implanted markers externally to the chest cavity. For example, FIG. 5 illustrates an embodiment of a stretch detection monitor device 540, which may be affixed or placed/positioned at least partially over the heart 501 of the patient on the surface of the chest, wherein the monitor may be configured to detect the position of the marker devices (not shown) and provide information regarding the same for atrial stretch monitoring purposes.

In some implementations, the atrial stretch detection monitor 540 can be affixed to the chest of the patient using an adhesive pad or other adhesive device, material, or mechanism. Alternatively, or additionally, the stretch detection monitor 540 may be held, strapped, placed, or otherwise positioned or secured to the chest of the patient at least partially over the patient's heart 501. The monitor device 540 may include battery power, or may operate using power received from a wired or wireless power source (not shown).

In some embodiments, implanted atrial stretch detection monitor devices may comprise one or more magnets, wherein the monitor device 540 is configured to detect the presence and/or location of the respective magnets. For example, the monitor device 540 may be configured or utilized to determine the distances between the markers (e.g., $d_{12}$, $d_{13}$, $d_{23}$). As the atrium stretches, the implanted marker devices may migrate with the stretching atrial tissue. As the marker devices move apart due to stretching, the monitor 540 may be configured or utilized to measure the change in distance between the markers, and/or the actual physical positions of the markers.

Figure 5:
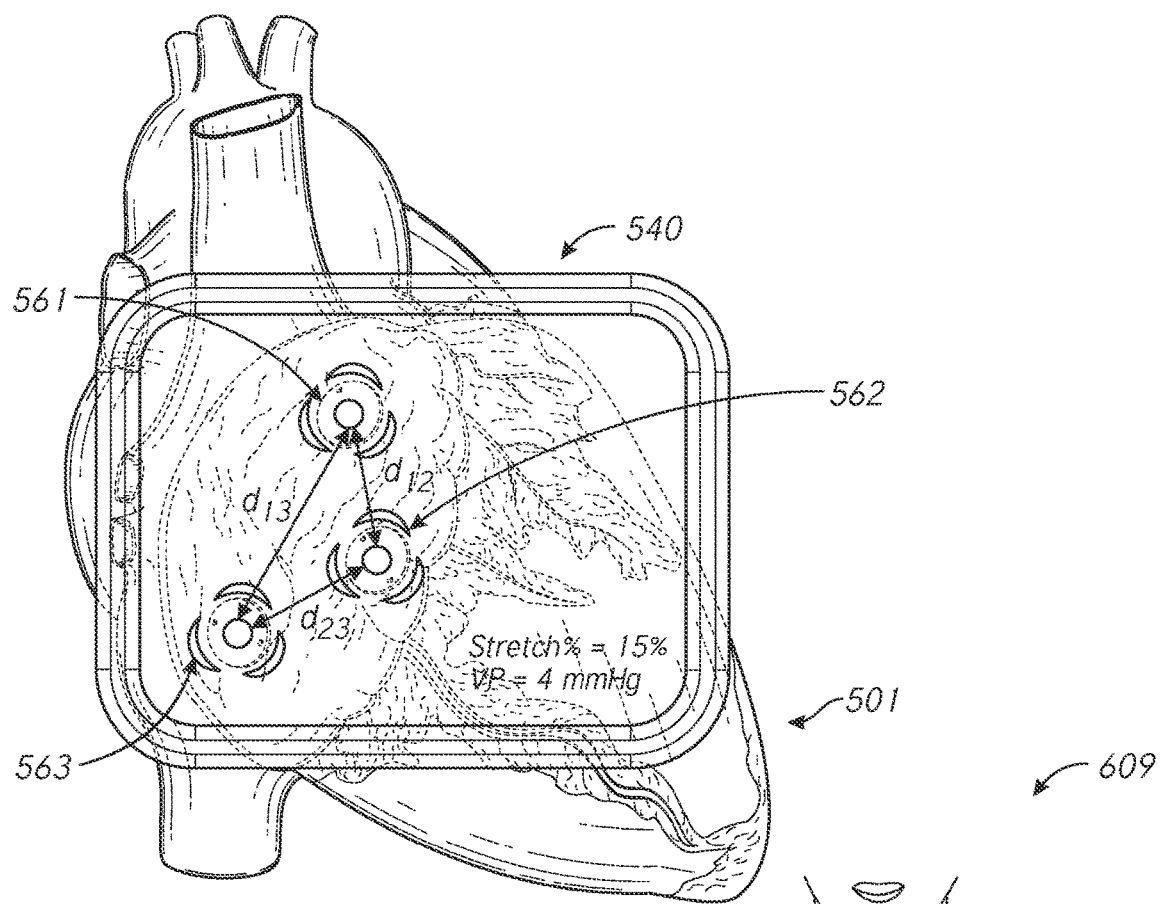
FIG. 5 illustrates a stretch detection monitor device in accordance with one or more embodiments.

The diagram of FIG. 5 illustrates visual indicators 561, 562, 563 associated with, and representative of, respective detected implanted marker devices. In some embodiments, such visual indication may be presented to the user via a display feature of the monitor device 540. Alternatively, the position and/or location information generated by the monitor 540 may be communicated to the operator in any other suitable or desirable manner, such as through the use of audio signaling, other visual signaling, data download, or the like. As shown, the monitor device 540 may provide information associated with stretch percentage and/or venous pressure. As referenced above, the monitor device 540 may implement metal-detection functionality, which may provide an electrical-impedance-based reading of the positions of the implanted marker devices.

Figure 6:
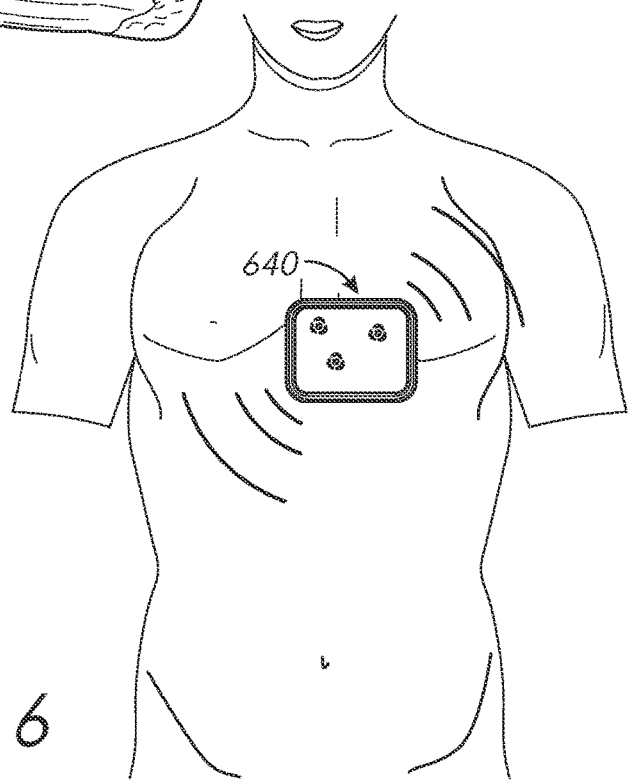
FIG. 6 illustrates a monitor device disposed on the chest of a patient in accordance with one or more embodiments.

FIG. 6 illustrates a monitor device 640 disposed on the chest of a patient 609 at least partially above or over an underlying heart (not shown) of the patient 609. The monitor device 140 may comprise alarm functionality for communicating to a user or system alerts or alarms indicating atrial stretch beyond a particular threshold, which may be a standard threshold, or may be customized for the particular patient. In certain embodiments, the monitor device 640 may be a peel-and-stick adhesive-backed pad device, as described herein, which may be conveniently applied to the chest of the patient 609 by positioning and applying pressure thereto.

Figure 8:
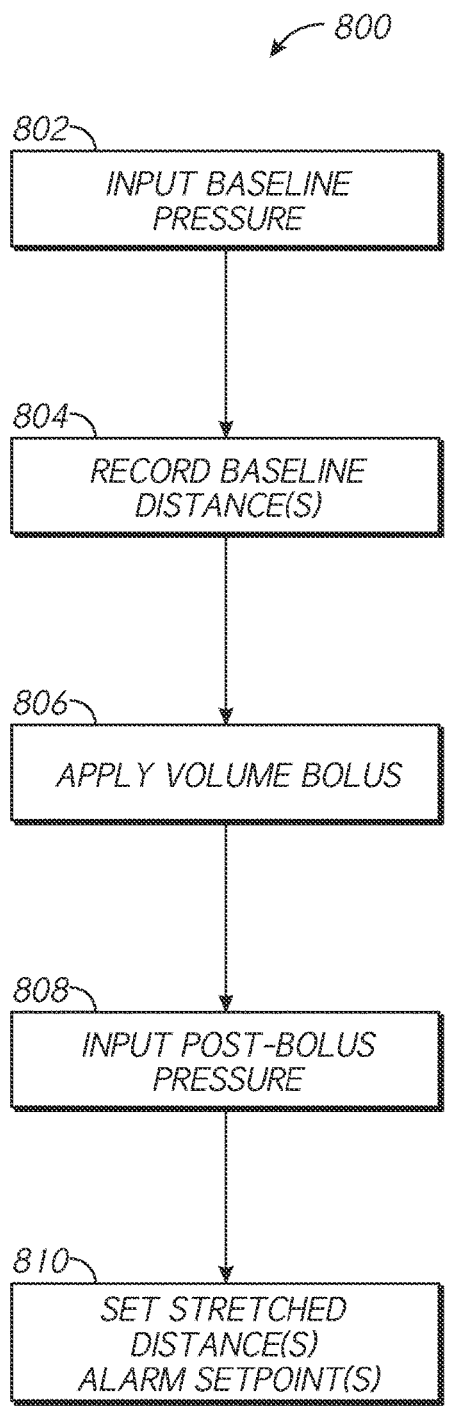
FIG. 8 illustrates a flow diagram for a process for calibrating an alarm threshold for atrial stretch in accordance with one or more embodiments.

The alarm-enabled monitor device 640 may be configured to indicate when excessive atrial stretching is detected or determined by the monitor 640 with respect to implanted marker devices inside the chest cavity of the patient, as described above. The monitor 640 may be configured to provide an alarm indication indicating excessive atrial stretch. Such indication may be audible, visible, and/or a combination of both. The thresholds at which an alarm is triggered may be associated with standard threshold levels, or may advantageously be determined or customized with respect to the particular patient 609. An example alarm setpoint threshold calibration process is illustrated in FIG. 8 and described in detail below.

Figure 7:
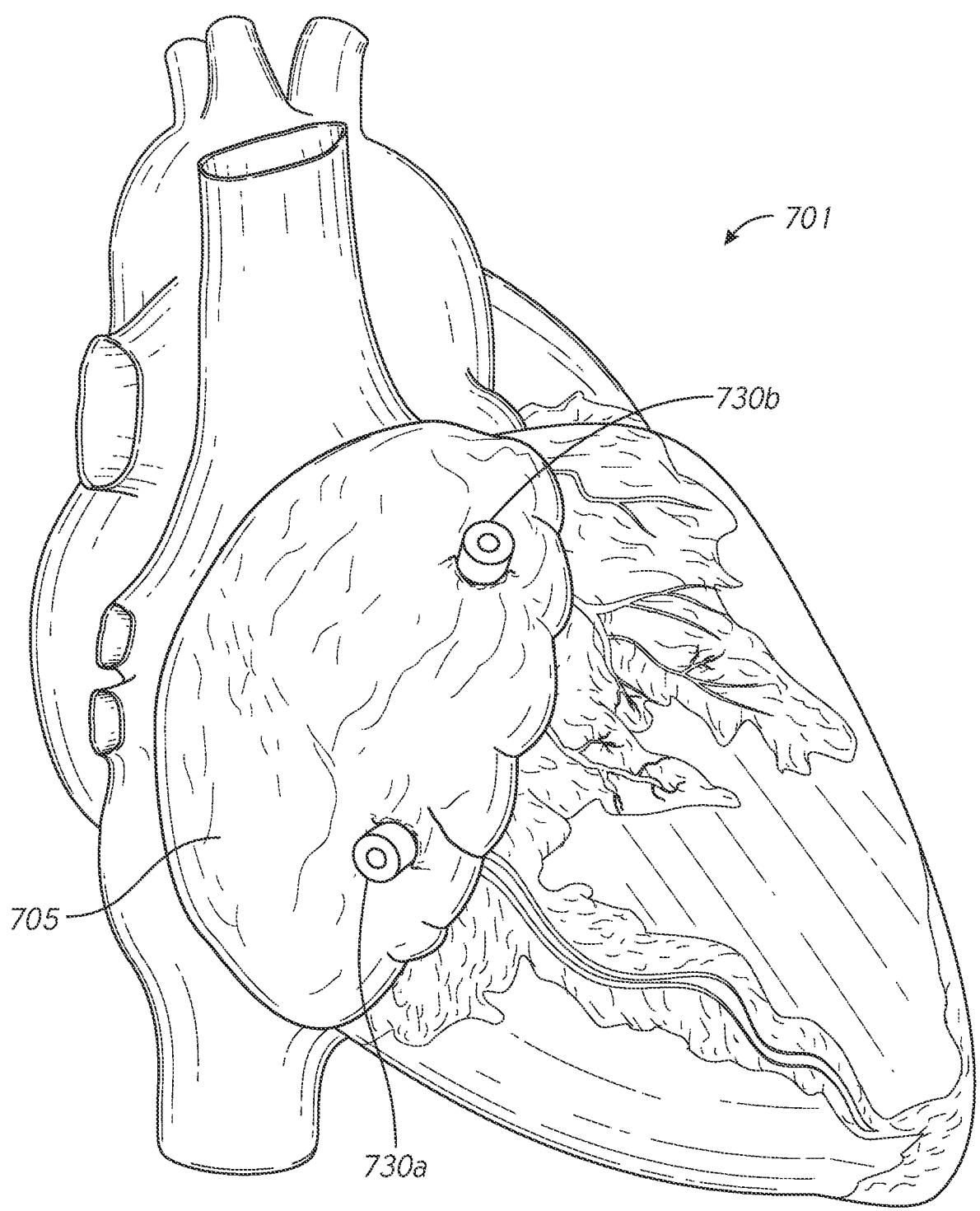
FIG. 7 illustrates a heart having implanted thereon a plurality of beacon devices in accordance with one or more embodiments.

FIG. 7 illustrates an embodiment of a heart 701 having implanted thereon a plurality of beacon devices 730a, 730b. In certain embodiments, at least one of the beacon devices (730a, 730b) may be configured to detect the presence and/or distance of another beacon device through any suitable or desirable means or mechanism, or alternatively may be detectable by an external monitor device. The implanted beacons 730a, 730b, may be implemented in combination with an external monitor device (not shown) similar to the monitor device 540 shown in FIG. 5 and described above. For example, the monitor device may be configured to detect the presence of, and/or distance between, the beacon devices based on the beacon sensing/detecting described above. In certain embodiments, the monitor (e.g., monitor 540 of FIG. 5) may be configured with an array of Hall effect sensors, which may comprise transducers configured to generate varied output voltages in response to the strength of a magnetic field detected. For example, with respect to a two-beacon magnetic detection embodiment, Hall effect sensors in the monitor device may produce a greater relative voltage output with respect to sensors positioned most closely to the implanted marker devices 730a, 730b. Therefore, the Hall effect sensors in the monitor device, where arranged in an array (e.g., a two-dimensional array) may provide information indicating positioning of the implanted beacon devices. In some embodiments, the monitor device may be configured with an array of up to 100, 1,000, 10,000, 100,000, 1,000,000, or more Hall effect sensors, which may advantageously provide suitable or desirable granularity with respect to the positioning identification of the implanted markers. In the array of Hall effect sensors, the particular sensor(s) that have the strongest signal output may generally be considered to align most closely with the position of the implanted marker/beacon devices. In some embodiments, each of the Hall effect sensors may be associated with one or more light source(s), such as light-emitting diode (LED) light source(s), wherein the brightness of the light associated with a particular sensor may indicate a closeness or proximity of the sensor to an implanted marker device. Therefore, visual inspection of the lighting array may advantageously provide a simplified visual indication of the locations of the implanted marker devices.

In some embodiments, implanted beacon marker devices may be configured to detect or sense one another. For example, a first implanted beacon device (e.g., 730a) may comprise a Hall effect sensor configured to detect a magnetic field of a magnet associated with a second beacon device (e.g., 730b). In such implementations, the Hall effect sensor beacon device may be configured to implement wireless transmission functionality, and may therefore comprise certain wireless transceivers circuitry for accomplishing the same.

In some implementations, the marker devices 730a, 730b may comprise radio-frequency identification (RFID) data storage and/or passive power functionality, such that the implanted beacon(s) function as an RFID tag that can be interrogated by an external RFID reader, which may be configured to send a signal to the marker device and/or read a response therefrom. The tag device may receive a power signal from the reader, wherein the tag device may utilize the power signal to facilitate transmission of data and/or other signals therefrom.

Implanted atrial stretch measurement/detection marker devices may be intended to be substantially permanent in their implantation. However, in certain implementations, previously-implanted marker devices may be retrievable in some manner. For example, atrial stretch detection/measurement marker devices may be retrievable through a chest tube, or other access channel into the chest cavity. However, the permanent nature of the implanted markers may advantageously allow for subsequent querying of the markers to determine long-term displacement of the markers over extended periods of time, such as after five years from surgery, or other time period. However, the permanent nature of the implants may introduce certain negative characteristics, such as the incompatibility of the conductive implanted devices with magnetic resonance imaging (MRI), and/or other procedures, which may undesirably dislodge such implants and/or cause physical damage or injury to the patient.

In certain embodiments, atrial stretch measurement implants in accordance with the present disclosure may comprise crystals, which may allow for the measurement of annular displacement through echolocation or other soundwave-based measurement functionality. For example, with implanted crystal devices, monitoring of atrial stretch may involve sending out soundwaves, wherein reflections from the implanted crystal devices may indicate position and/or relative distance of the implanted crystal devices.

FIG. 8 illustrates a flow diagram 800 for calibrating an alarm threshold for atrial stretch in accordance with one or more embodiments. The process 800 may be implemented to determine one or more alarm setpoints for triggering an alarm or notification in connection with stretch-detection devices or methods disclosed herein.

Figure 9A:
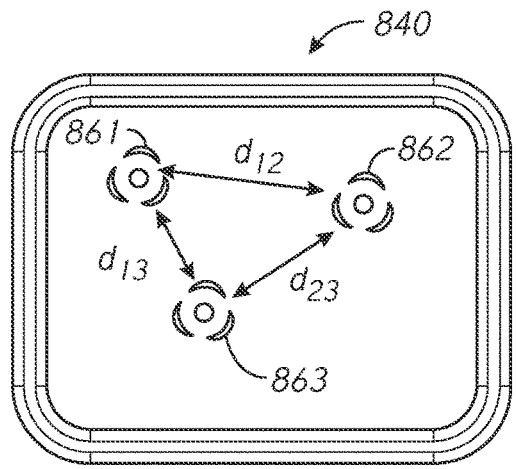
FIG. 9A illustrates a stretch detection monitor device in accordance with one or more embodiments.

The process 800 may be implemented in connection with a patient having a plurality of atrial stretch detection markers implanted on the surface of one or more atria of the heart of the patient. Furthermore, the process 800 may be implemented in connection with a stretch detection monitor device 840, as shown in FIG. 9A, which may indicate the positions and/or relative positions of the marker devices implanted on the heart, as shown and described in connection with FIGS. 5 and 6. In some embodiments, the monitor device 840 may present visual indicators, such as blinking or strobing lights (e.g., LED lights), and/or audible noise indication, indicating that a stretch limit has been reached. Furthermore, the monitor device 840 may comprise a visual display 850 that is configured to present stretch measurement values, such as stretch percentage, and/or one or more other indications that a stretch limit has been exceeded. In certain embodiments, the monitor device 840 comprises a peel-and-stick pad, or a strap-on pad. In the illustrated embodiment, the display 850 displays icons 861, 862, 863 that are aligned with and/or represent the positions of respective implanted markers (not shown). The display icons 861, 862, 863 indicate icon-to-icon distances $d_{12}'$, $d_{23}'$, $d_{13}'$, which may represent distances between detected markers. The distances $d_{12}'$, $d_{23}'$, $d_{13}'$ may be the actual distances between the detected markers, or may provide a scaled representation of the distances between the detected marker devices.

At block 802, the process 800 involves determining and/or inputting a baseline jugular vein pressure of the patient 805. As one illustrative example, the initial pressure may be determined to be approximately 44 mmHg, which may provide the baseline pressure for calibration in accordance with the process 800. The pressure reading may be determined in any suitable or desirable way. At block 804, the process 800 involves recording the baseline distance(s) between the markers and/or position of the implanted markers, as associated with the baseline pressure determined at block 802. The monitor 840 shown in FIG. 9A shows the baseline positioning of the monitored implant devices as represented by the icons 861, 862, 863 that represent the detected positions of the implanted marker devices (not shown).

Figure 9B:
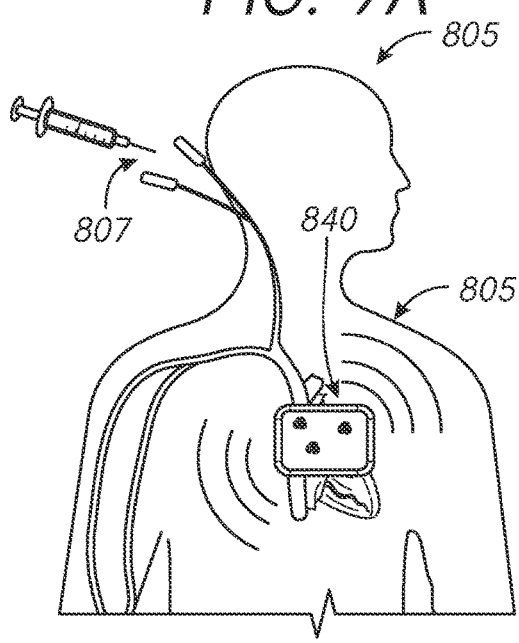
FIG. 9B illustrates a patient receiving an administration of fluid in accordance with one or more embodiments.

Generally, when atrial stretch marker devices are implanted in a patient, there may be access to a central venous line of the patient, which may allow for relatively convenient introduction of intravenous (IV) fluid into the patient. At block 806, the process 800 involves administering a bolus of fluid, such as saline fluid or the like, into the vascular system of the patient 805. Such bolus may be any suitable or desirable volume, such as hundred milliliters, or other volume bolus. FIG. 9B illustrates the administration of fluid through an IV line 807 into the patient 805, as described at block 806.

At block 808, the process 800 involves inputting the post-bolus pressure reading of the patient. For example, such reading may indicate the jugular vein pressure, or pressure of another blood vessel, within the patient 805 after the administration of the bolus in connection with block 806.

Figure 9C:
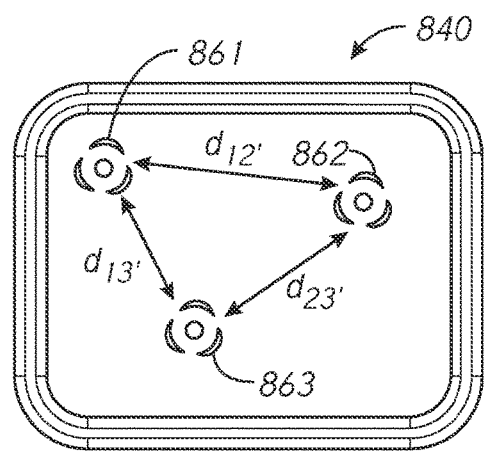
FIG. 9C illustrates a stretch detection monitor device in accordance with one or more embodiments.

At block 810, the process 800 involves determining the distance/stretch measurement of the implanted markers after administration of the bolus. For example, the markers may have undergone some amount of migration away from one another in one or more directions due to atrial stretching induced by the increased pressure in the atria associated with the administration of the fluid bolus. FIG. 9C illustrates the monitor device 840, wherein the display icons 861, 862, 863 show increased respective distances $d_{12}'$, $d_{23}'$, $d_{13}'$ between the detected marker devices due to atrial stretching. The determined/measured distances and/or amount of stretch measured in connection with block 810 may serve as a basis for setting the alarm set point for the patient. That is, the extent of the stretching and migration of the implanted markers experienced in response to administration of the fluid bolus may serve as a limit for stretching of the atria or atrium that triggers notification or alarm generation by the monitor 840 or other system component. Therefore, the process 800 may allow for customized alarm setpoints for different patients. As described above, alarms associated with excessive stretching or migration of the markers beyond the set alarm setpoints/limits may be audible, visible, or combination thereof.

Certain embodiments disclosed herein provide for atrial stretch measurement using devices configured to indicate mechanical displacement with respect to a plurality of areas of an atrium of a heart. For convenience, certain stretch-measurement devices disclosed herein are referred to as stretch-measurement probes. The term "probe" is used herein according to its broad and ordinary meaning, and may refer to any type of measurement tool, as described.

Stretch-measurement probes disclosed herein may be used to measure atrial stretch, or other stretch or displacement associated with an organ of a patient. Such devices may advantageously provide an indication of atrial stretch in connection with the stretching of an atrium of the heart. Furthermore, such indication may advantageously be accessible and/or visible external to the patient, while at least a portion of the stretch-measurement probe is disposed within a chest cavity of the patient, and in particular, in proximity to the surface of one or more atria of the heart of the patient.

Figure 10:
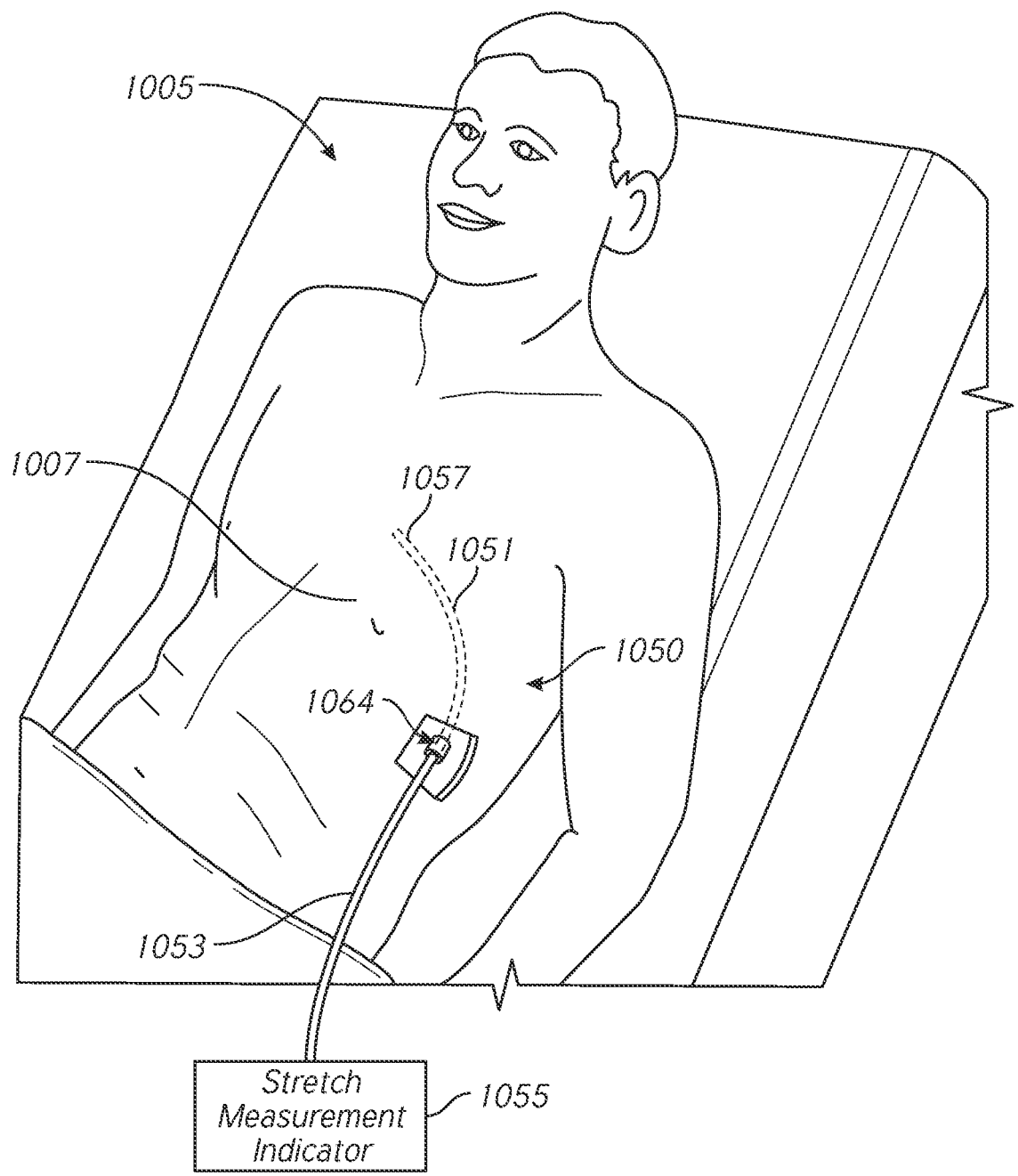
FIG. 10 illustrates a patient having a stretch-measurement probe inserted/disposed at least partially in a chest cavity in accordance with one or more embodiments.

Mechanical stretch-measurement probes in accordance with the present disclosure may include a distal portion, which may be directly affixed at one or more points to the surface of the atrium. FIG. 10 illustrates a patient 1005 having a stretch-measurement probe inserted/disposed at least partially in a chest cavity 1007 of the patient 1005, such as through a chest tube or other access channel 1064. In certain embodiments, the stretch-measurement device 150 may be fed through a small opening in the chest/torso of the patient 1005. For example, similar to cardiac pacing leads that may be associated with certain cardiac surgeries, the proximal portion 1053 of the stretch-measurement probe 1050 may exit the chest wall of the patient for external access thereto. The stretch-measurement probe 1050 may be removable from the chest cavity 1007 of the patient 1005 at some point in time after surgery, such as a period of 5-10 days post operation.

The distal portion 1057 of the stretch-measurement probe 1050 may be approximated to the surface of an atrium of the heart during, for example, open-heart cardiac surgery or other thoracic surgery or operation. The distal portion 1057 may be part of an internally-disposed portion 1051 of the stretch-measurement probe 1050, while a remaining portion 1053 may generally be disposed externally to the patient when the distal portion is implanted in the chest cavity 1007. The proximal portion 1055 of the stretch-measurement probe 1050 may provide a stretch measurement indicator mechanism or feature, as described in greater detail below.

Figure 11:
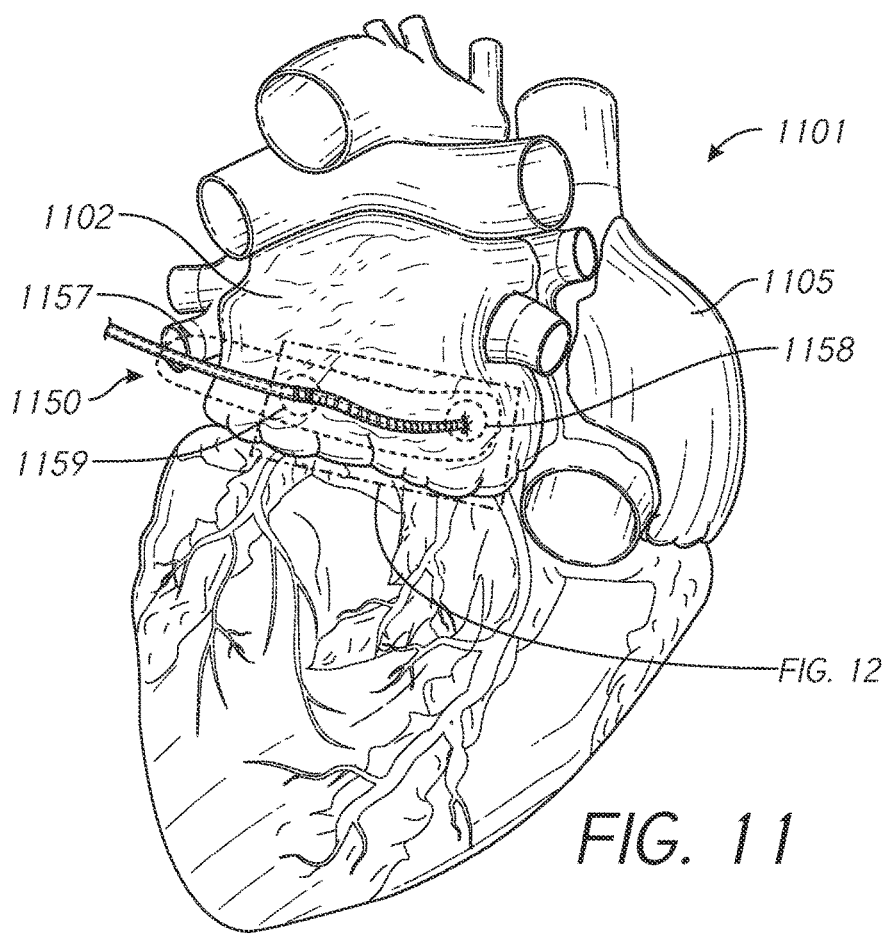
FIG. 11 illustrates a heart having a stretch-measurement probe affixed thereto in accordance with one or more embodiments.

FIG. 11 illustrates a heart 1101, wherein a distal portion 1157 of a stretch-measurement probe 1150 is affixed to the surface of, for example, the lateral side of the left atrium 1102 of the heart 1101. Although certain embodiments are disclosed herein in the context of implantation or fixing of the distal end portion of a stretch-measurement probe to the left atrium of the heart, it should be understood that the principles and features disclosed herein are applicable to stretch measurement, and implantation of a stretch-measurement probe, on or with respect to the right atrium of the heart.

In certain implementations, the stretch-measurement probe 1150 may be approximated to the atrium 1102 of the heart 1101 during an open-chest operation, wherein the distal portion 1157 of the probe 1150 may be surgically attached to the surface of the atrium 1102 and/or laid over the surface of the atrium. The distal portion 1157 of the probe 1150 may be secured so that it is substantially fixed at one or more points thereof to the atrium surface. In some implementations, the distal portion 1157 is secured in such a way as to be removable at a later time. The removability feature(s) of the measurement device advantageously provide a convenient mechanism for measuring tissue stretching, while not requiring permanent implants or prolonged maintenance of implanted device(s) in the body, which can improve long-term health prospects compared to permanent or long-term implant devices. A proximal portion of the probe (not shown) may at least partially stick out of the body cavity, such as out through a chest tube implanted in the chest of the patient, or may alternatively be retrievable and/or accessible through a separate dedicated passage through the chest wall or other thoracic region.

Figure 12:
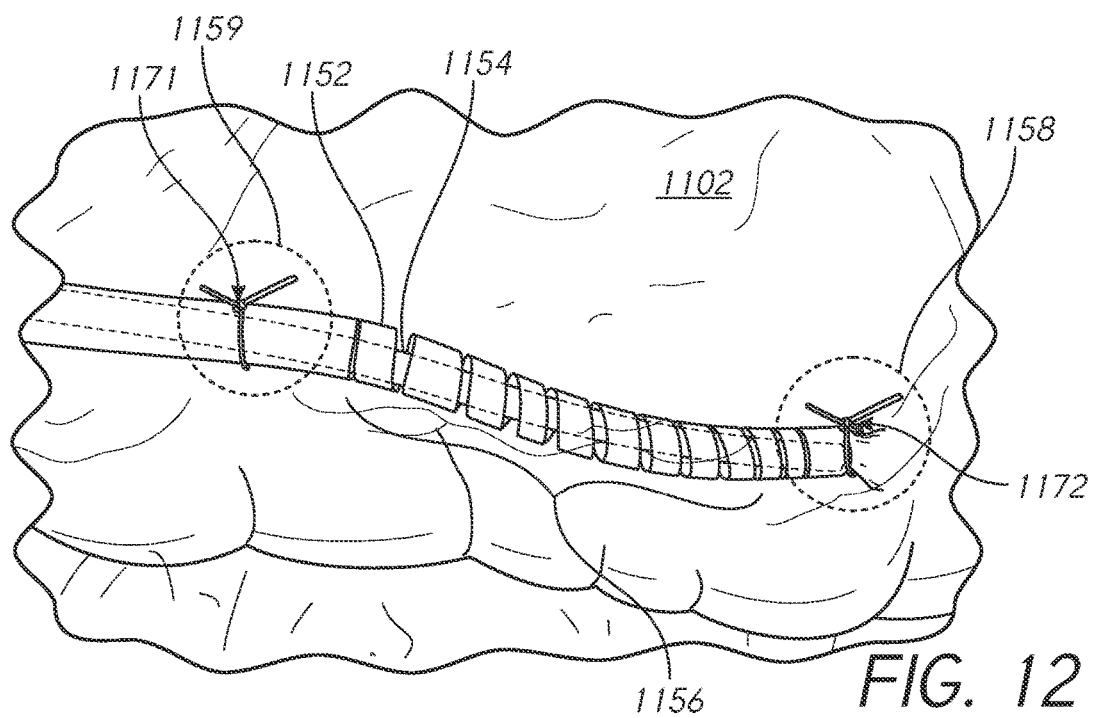
FIG. 12 provides a close-up view of a portion of the image of FIG. 11 in accordance with one or more embodiments.

The stretch-measurement probe 1150 may advantageously allow for direct measurement of atrial stretch between fixture points 1158, 1159. Description herein of fixture points of a proximal portion of a stretch-measurement probe may refer to atrial tissue fixture points and/or point or portions of the probe device that are fixed to the atrial tissue. The fixture points illustrated in FIG. 11 are shown in greater detail in the close-up illustration of FIG. 12. FIGS. 11 and 12 provide sample placements of the distal portion 1157 of the measurement probe 1150. In the illustrated embodiment, two sutures 1171, 1172 are utilized to secure the two points 1158, 1159 of the probe 1150 to proximal areas of the atrium surface tissue. Although particular sizes and dimensions are illustrated in connection with the probe 1150 shown in FIGS. 11 and 12, it should be understood that stretch-measurement probes in accordance with the present disclosure may have any suitable or desirable shape, size, and/or dimensions. For example, in some patients, a stretch-measurement probe in accordance with the present disclosure may have a diameter and/or length dimension comparable to a traditional cardiac pacing lead.

Although sutures 1171, 1172 are shown in FIG. 12, it should be understood that any tissue attachment mechanism or feature may be implemented to secure the respective portions of the stretch-measurement probe 1150 to the surface of the atrium. In some embodiments, sutures used to secure the probe 1150 to the atrium may remain tied to the atrium wall after removal of the stretch-measurement probe 1150 from the chest cavity.

The distal portion 1157 of the stretch-measurement probe 1150 includes an exterior sleeve component 1152, as well as an interior rod component 1154, which may be disposed within the sleeve 1152. In certain embodiments, the inner rod 1154 may be fixed to the outer sleeve 1152 at or near the end 1158 of the probe 1150. For example, the distal end of the inner rod 1154 may be glued or attached to the distal end of the outer sleeve 1152. Although secured to the end portion 1158 of the outer sleeve 1152, the inner rod 1154 may otherwise be free to float and/or move radially within the sleeve 1152.

The distal portion 1157 further includes an expandable stretch feature 1156, which may advantageously allow for the longitudinal expansion of the outer sleeve 1152 at least partially independently of the inner rod portion 1154. Due to the attachment of the inner rod 1154 to the outer sleeve 1152 at the distal end 1158 of the stretch-measurement probe, and the expandable stretch feature 1156, which allows for the outer sleeve 1152 to stretch in a longitudinal dimension independently of the inner rod 1154, the fixed portion 1159 of the outer sleeve 1152 may be permitted to become displaced in the longitudinal direction of the measurement probe independently of the inner rod 1154. Therefore, while the body of the outer sleeve 1152 may slide longitudinally away from the distal end 1158, the inner rod 1154 may generally remain in a fixed relative position with respect to the distal end portion 1158 of the stretch-measurement probe 1150.

In certain embodiments, the expansion feature 1156 of the outer sleeve 1152 presents relatively little resistance to expansion. Where the outer sleeve 1152 is sutured or otherwise secured to the first and second points/areas 1159, 1158 of the surface of the atrium, the expansion feature 1156 may allow for the outer sleeve 1152 to expand as the atrium stretches and expands between the attachment points 1158, 1159. Therefore, the stretch-measurement probe 1150 may act as a strain gauge, providing a stretch measurement indication reflected in the relative movement of the outer sleeve 1152 to the inner rod 1154 that corresponds to atrial stretch associated with the atrium 1102.

In some embodiments, the expandable stretch feature 1156 of the outer sleeve 1152 may comprise a helical soft-spring form, which may be formed by cutting the outer sleeve 1152 in a helical fashion around the circumference thereof. The expandable stretch feature 1156 may advantageously be sufficiently flexible, stretchy and/or compliant to allow for free movement thereof with the stretching of the atrium, without substantially affecting or pulling on the tissue thereof.

Figure 13A:
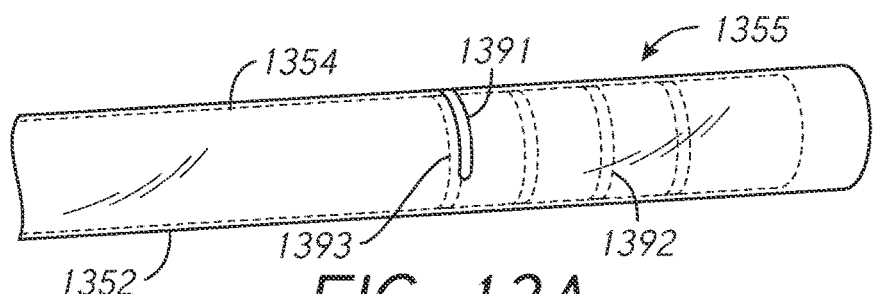
FIGS. 13A and 13B illustrate a proximal end portion of a stretch-measurement probe in accordance with one or more embodiments.
Figure 13B:
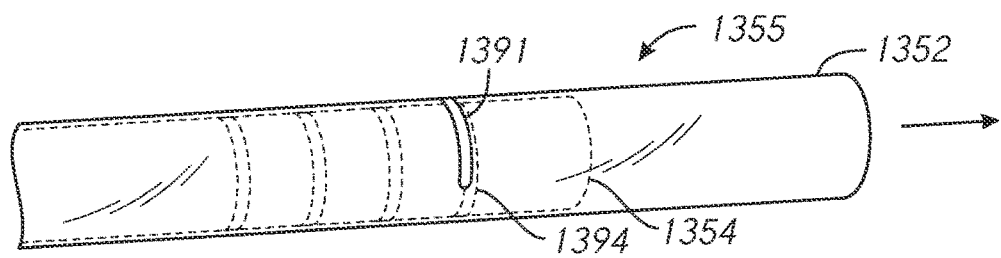

FIGS. 13A and 13B illustrate a proximal end portion 1355 of a stretch-measurement probe in accordance with one or more embodiments. As described above, where properly fixed to the surface of the atrium, a stretch-measurement probe may allow for the independent longitudinal movement and/or expansion of an outer sleeve component 1352 relative to an internal rod component 1354. Such relative movement may be visibly apparent at the proximal end of the stretch-measurement probe. For example, the outer sleeve 1352 may expand and elongate longitudinally away from the distal end of the stretch-measurement probe, while the inner rod 1354 may remain in a relatively-fixed position with respect to the distal end portion of the stretch-measurement probe. Therefore, the proximal end portion 1355 may reveal such relative expansion/movement between the outer sleeve 1352 and the rod 1354.

In some embodiments, the proximal end portion 1355, or other portion of the stretch-measurement probe 1350, may include one or more markers or other visual indicators 1391 on the outer sleeve component 1352, as well as one or more markers or other visual indicators 1392 on the inner rod component 1354. Therefore, as the outer sleeve 1352 expands away from the distal end portion of the stretch-measurement probe, while the inner rod portion 1354 remains in a fixed relative position with respect to the distal end portion stretch-measurement probe, the relative positioning of the outer marker 1391 with respect to the inner marker 1392 may change, thereby providing an indication of atrial stretch. For example, FIG. 13A shows the proximal end portion 1355, wherein an outer marker 1391 is substantially aligned with a first marker 1393 of the inner rod 1354. After the atrium stretches, causing the outer sleeve 1352 to expand, the outer marker 1391, as shown in FIG. 13B, may become aligned with a second marker 1394, as opposed to the initial marker 1393. The amount of movement of the outer and inner markers relative to one another may indicate an amount of atrial stretch measured.

In some implementations, atrial stretch of approximately 4-5 mm may be considered clinically significant. Therefore, it may be desirable for the stretch-measurement probe and/or measurement indicator markers associated therewith to be sensitive enough to indicate measurement of 4-5 mm, or less. Such stretch may generally be associated with the circumferential stretch of the atrium. The stitch-to-stitch displacement at the distal end of the stretch-measurement probe of the outer sleeve portion may advantageously be directly translated to the relative displacement of the outer sleeve 1352 at the proximal end of the search measurement probe. In some embodiments, greater than 90% of the stretch of the atrium between the suture points is reflected in the displacement of the proximal end of the outer sleeve 1352 of the stretch-measurement probe.

Figure 14:
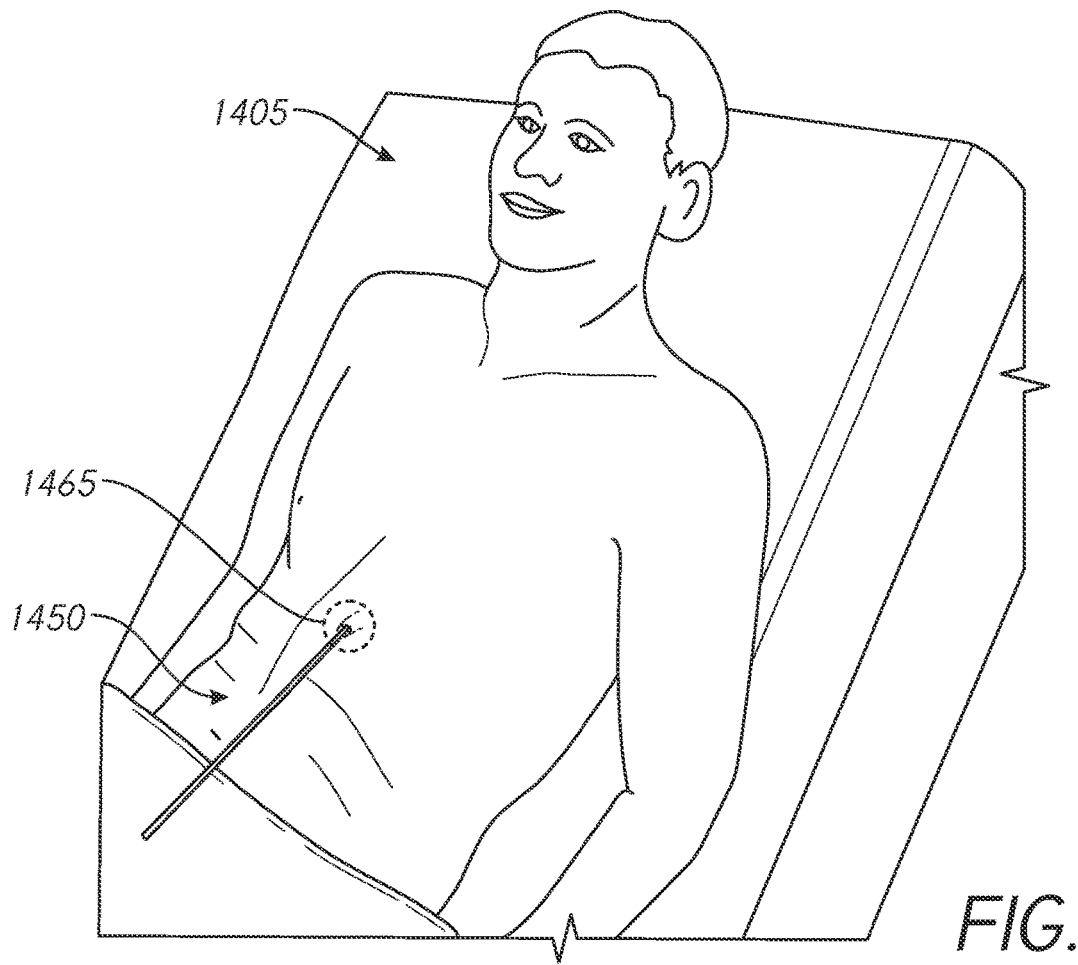
FIG. 14 illustrates a torso and/or chest of a patient having an access point for retrieval of a stretch-measurement probe in accordance with one or more embodiments.

FIG. 14 illustrates a torso and/or chest of a patient having an access point 1465 for retrieval of a stretch-measurement probe 1450 in accordance with some implementations. In some implementations, a stretch-measurement probe in accordance with the present disclosure may be removable in a similar manner to pacemaker leads, which may generally be removable by pulling through the chest wall through an access point. In order to reduce the amount of discomfort experienced by a patient having a stretch-measurement probe removed therefrom, it may be desirable for the stretch-measurement probe 1450 to have a diameter of approximately 2 mm or less. The stretch measurement probe may advantageously be removable from the body of the patient.

Figure 15:
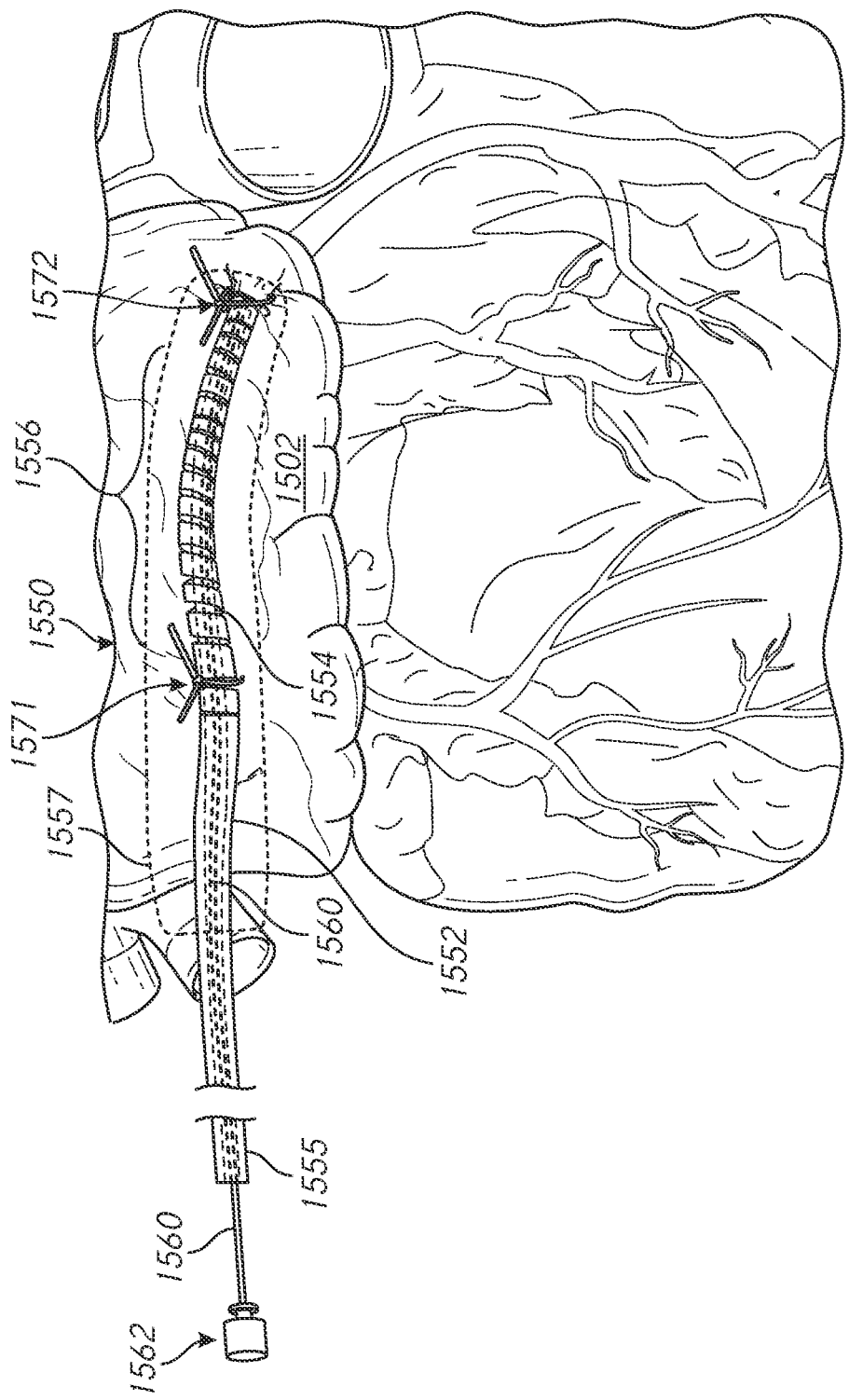
FIG. 15 illustrates a distal portion of a stretch-measurement probe sutured to the surface of an atrium of a heart of a patient in accordance to one or more embodiments.

FIG. 15 illustrates a distal portion 1557 of a stretch-measurement probe 1550 sutured to the surface of an atrium 1502, such as the left atrium, of a heart of a patient in accordance to one or more embodiments. In particular, the distal portion 1557 is illustrated as being sutured to the surface of the atrium 1502 at two suture points, a first suture point 1571 and a second suture point 1572. Generally, a stretch expansion feature 1556 may be associated with an outer sleeve component 1554 of the stretch-measurement probe 1550 in a region between the first suture point 1571 and the second suture point 1572.

In the illustrated embodiment, the stretch-measurement probe 1550 may be released from attachment to the surface of the atrium 1502 through the use of a pull-wire release feature comprising a pull wire component 160, which may be disposed at least partially within the outer sleeve 1552, but external to the inner rod 1554. Through the use of the pull wire release mechanism, the stretch-measurement probe 1550 may be anchored to the surface of the atrium 1502 temporarily, wherein the probe 1550 may become detached from the surface of the atrium through engagement of an external portion or feature 1562 of the pull-wire release assembly. Therefore, the probe 1550 may advantageously be removable, thereby providing desirable short- or long-term comfort and health prospects for the patient.

In certain embodiments, the wire 1560 (e.g., metal wire) of the pule-wire release mechanism may be disposed within the stretch-measurement probe 1550, such that the sutures are threaded around the wire 160. For example, when suturing the probe 1550 to the surface of the atrium 1502, the surgeon may thread the sutures around the wire 1560 through an opening or slit in the outer sleeve 1554, and further suture through the tissue of the atrium. Alternatively, the wire 1560 may be threaded between the suture and the outer sleeve, within the outer sleeve, in order to tie the outer sleeve 1552 and wire 1560 to the tissue via the suture. In order to allow for passage of the suture around the wire 1560 within the outer sleeve 1552, the outer sleeve 1552 may comprise one or more scallop features, which may comprise cut-outs, grooves, slits, shoulders, or other features allowing for passage of the suture through the outer sleeve. The scallop features advantageously may be tight enough longitudinally to prevent sliding of the outer sleeve 1552 with respect to the suture 1571.

In order to detach the probe 1550 from the surface of the atrium 1502, the pull wire 160 may be withdrawn from the distal portion 1557 of the probe 1550, such as by pulling a proximal end member 1562 associated with the wire 1560 away from the atrium of the patient. For example, the proximal end of the pull-wire release system may be accessible through a proximal end 1555 of the stretch measurement probe 1550 and/or outer sleeve 1552. In some implementations, the pull-wire release mechanism may break the sutures 1571, 1572. Although a particular pull-wire release system is illustrated in FIG. 15, release of a stretch-measurement probe from the surface of the atrium may be achieved through electrical detachment, or through the use of bioresorbable sutures that may breakdown or dissolve over time, thereby permitting release and retrieval of the probe. Once the pull-wire release, or other detachment mechanism, has been used to detach the stretch-measurement probe 1550, the entire stretch-measurement probe may be withdrawn from chest cavity of the patient.

Figure 16:
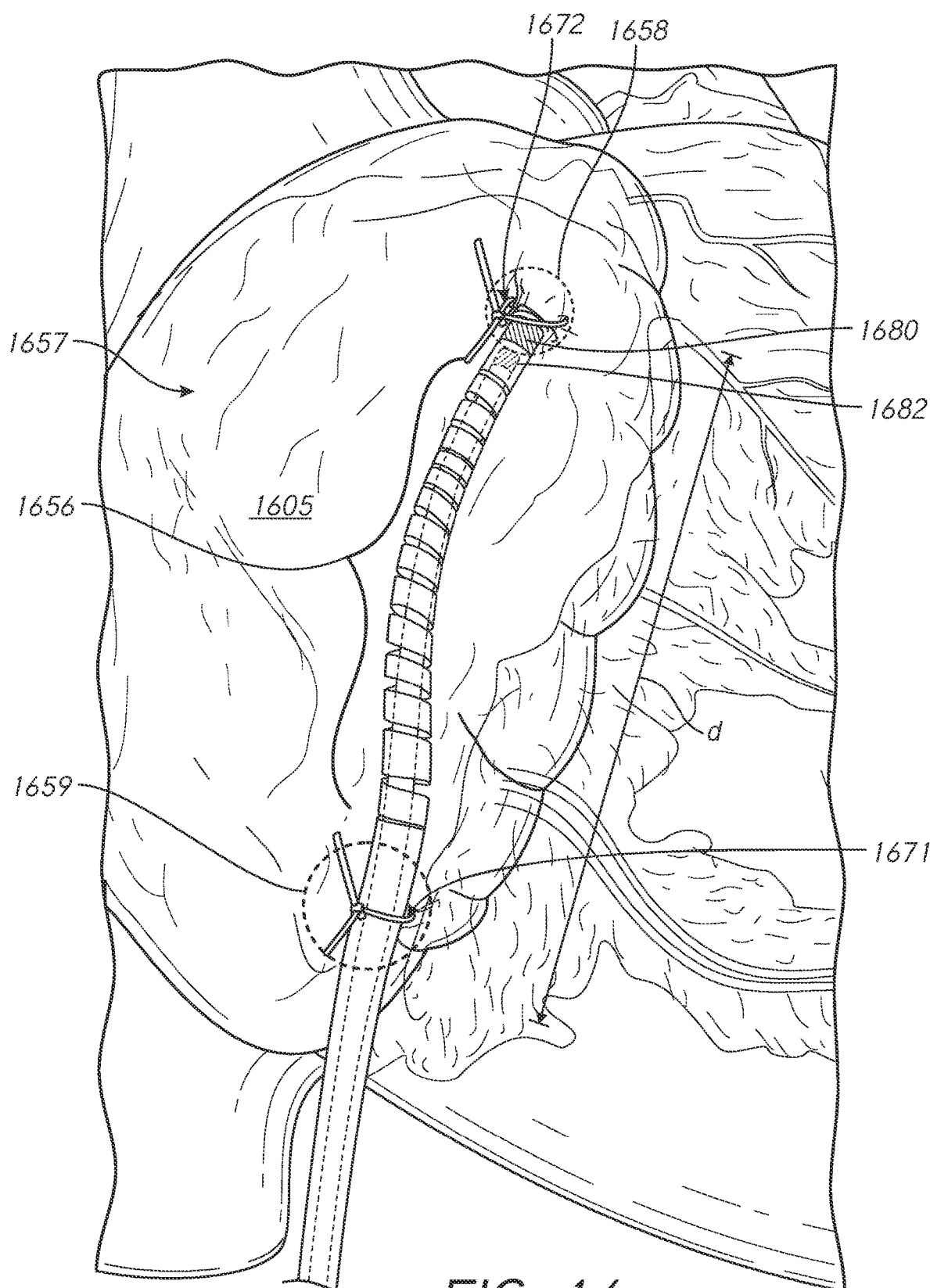
FIG. 16 illustrates an electronic stretch-measurement probe in accordance with one or more embodiments.

FIG. 16 illustrates an embodiment of an electronic stretch-measurement probe 1650 in accordance with one or more embodiments. The electronic stretch-measurement probe 1650, and in particular the distal portion 1657, may be attached to, for example, the right atrium 1605 of a heart in some embodiments, such as on the anterior side of the right atrium. Alternatively, the electronic stretch-measurement probe 1650 may be attached to the left atrium (not shown), such as on a lateral side of the left atrium. FIG. 16 shows a close-up view, which may be similar in certain respects to the close-up view of the mechanical stretch-measurement probe 1250 shown in FIG. 12 and described above. For example, the view of FIG. 16 illustrates a distal portion 1657 of the stretch-measurement probe 1650, which may be secured to one or more portions of the atrium surface. For example, the probe 1650 may be secured to the atrium surface at two points, such as at the illustrated regions 1659, 1658. For example, the first attachment point 158 may be associated with, or proximate to, a distal end 1658 of the distal portion 1657, while the second attachment point 1659 may be a distance d longitudinally offset or removed from the distal end 1658.

The stretch-measurement probe 1650 includes an outer sleeve component 1652, as well as an inner rod component 1654, which may be similar in certain respects to the corresponding features of the mechanical stretch-measurement probes described above. Furthermore, the outer sleeve 1652 may incorporate a stretch expansion feature 1656 between the attachment points 1658, 1659, which may allow for longitudinal expansion or stretching of the outer sleeve 1652. In certain embodiments, the electronic stretch-measurement probe 1650 may incorporate a pull-wire release feature to allow for removal of the probe post-operatively, as described above in detail in connection with mechanical stretch-measurement probes. The removability feature(s) of the electronic stretch-measurement probe advantageously provides a convenient mechanism for measuring tissue stretching, while not requiring permanent implants or prolonged maintenance of implanted device(s) in the body, which can improve long-term health prospects compared to permanent or long-term implant devices.

The electronic stretch-measurement probe 1650 may be operatively placed for direct measurement of atrial stretch, and may be attached to the atrium surface 1605 using two stitches 1671, 1672. In some embodiments, the distal end of the outer sleeve 1652 is coupled to a first sensor element 1680, and the distal end of the inner rod 1654 is coupled to a second sensor element 1682. The first and second sensor elements 1680, 1682, may be configured such that the voltage output of one of the sensor elements changes in relation to the distance between the first and second sensor elements. For example, where one sensor element comprises a magnet, the other sensor element may comprise an electromagnetic sensor, such as a Hall effect sensor, or the like. Therefore, the voltage output of the sensor may be indicative of the displacement of the sensor element 1682 from the sensor element 1680. In some embodiments, the sensor element 1680 at the distal end 1658 of the outer sleeve 1652 is an electrical sensor, such as a Hall effect sensor, while the sensor element 1682 at the distal end of the rod portion 1654 comprises a magnet or other sensor element that may be sensed by the sensor element 1680. Alternatively, in some embodiments, the sensor element 1680 comprises a magnet, or other element that can be electrically sensed, while the sensor element 1682 comprises an electromagnetic sensor, such as a Hall effect sensor, or the like.

In some embodiments, the inner rod 1654 is not fixed to the end portion 1658 of the outer sleeve 1652, but may be fixed at the second attachment points 1659 of the outer sleeve 1652, such that stretching of the atrium surface 1605 between the two attachment points causes the outer sleeve 1652, and in particular the expansion feature 1656 of the outer sleeve 1652, to stretch or expand between the two attachment points or sutures. Therefore, where the inner rod 1654 is fixed to the outer sleeve 1652 at a point at or beyond (in a longitudinal direction moving away from the distal end point 1658) the second attachment point 1659, but not attached or fixed to the outer sleeve 1652 between the second attachment point 1659 and the distal end attachment point 1658, stretching or expansion of the expansion feature 1656 of the outer sleeve 1652 may generally result in the distal end of the inner rod portion 1654 being drawn away from the distal end 1658 of the outer sleeve 1652. The stitch-to-stitch displacements of the outer sleeve 1652 may be reflected in a voltage drop at the sensor element 1682 and/or sensor element 1680 caused by the increased distance between the sensor elements as the distal end of the inner rod 1654 is drawn away from the distal end of the outer sleeve 1652.

In some embodiments, certain electrical wiring or leads may be housed within the outer sleeve 1652 and/or inner rod 1654, and connect to the sensor element 1682 associated with the inner rod 1654, or to the sensor element 1680 associated with the outer sleeve 1652. Such wiring may allow for voltage levels associated with the sensor element(s) to be read externally to the chest cavity of the patient. Such voltage readings may advantageously provide a relatively accurate measurement of atrial stretch.

Removal of the stretch-measurement probe 1650 may be achieved in a manner similar to those described above in connection with mechanical stretch-measurement probes. For example, the electronic stretch-measurement probe 1650 may be withdrawn, such as after implementation of a wire or other detachment mechanism, through a chest tube or other chest or torso access conduit/channel. In certain embodiments, the dimensions of the sensor elements, such as Hall effect sensors or the like, have a diameter or width dimension of approximately 2 mm or less, which may advantageously allow for the stretch-measurement probe 1650 to have a relatively small diameter, thereby reducing the discomfort to the patient associated with removal of the probe 1650.

The electronics of the electronic stretch-measurement probe 1650 may advantageously allow for desirable resolution with respect to stretch measurement readings, and in some implementations, may provide improved resolution compared to mechanical stretch-measurement probes. Furthermore, the electrical readings generated by the electronic stretch-measurement probe 1650 may allow for noise associated with pumping of the chambers of the heart and/or pacing of the heart to be filtered out, thereby providing improved measurement of atrial stretch. For example, the sensor element(s), while implanted, may pick up certain information associated with heartrate and/or other waveforms associated with atrial tissue displacement. In some implementations, a mean value of displacement of the sensor element 1680 from the sensor element 1682 may be used to determine atrial stretch. The sensor element 1682 and/or sensor element 1680 may generally be insulated, such as encapsulated or enclosed in polymer or other protective material. Furthermore, electrical wires and/or leads running to the sensor element(s) may be encapsulated in insulating material.

The present disclosure describes various means for measuring stretching, dilation, expansion, contraction, compression, shrinking and/or other modification of tissue or change in relative distance between two or more points or areas of tissue, such as atrial tissue. In certain embodiments, atrial stretch measurement implants and devices in accordance with the present disclosure comprise crystal devices, which may allow for the measurement of annular displacement through echolocation or other soundwave-based measurement functionality, or through other means. For example, with implanted crystal devices, monitoring of atrial stretch may involve sending out soundwaves, wherein reflections from the implanted crystal devices may indicate position and/or relative distance of the implanted crystal devices.

In some embodiments, sonomicrometry is implemented as a mechanism for measuring tissue modification, such as atrial tissue stretch. Processes for sonomicrometry are disclosed in "A Simple Portable Sonomicrometer," Kardon, M. B., Stegall, H. F., & Stone, H. L. 1966 (http://www.dtic.mil/dtic/tr/fulltext/u2/641571.pdf), the disclosure of which is hereby incorporated by reference in its entirety. Sonomicrometry generally involves the measurement of the distance between piezoelectric crystals based on the speed of acoustic signals through the medium they are disposed or embedded in.

Figure 17:
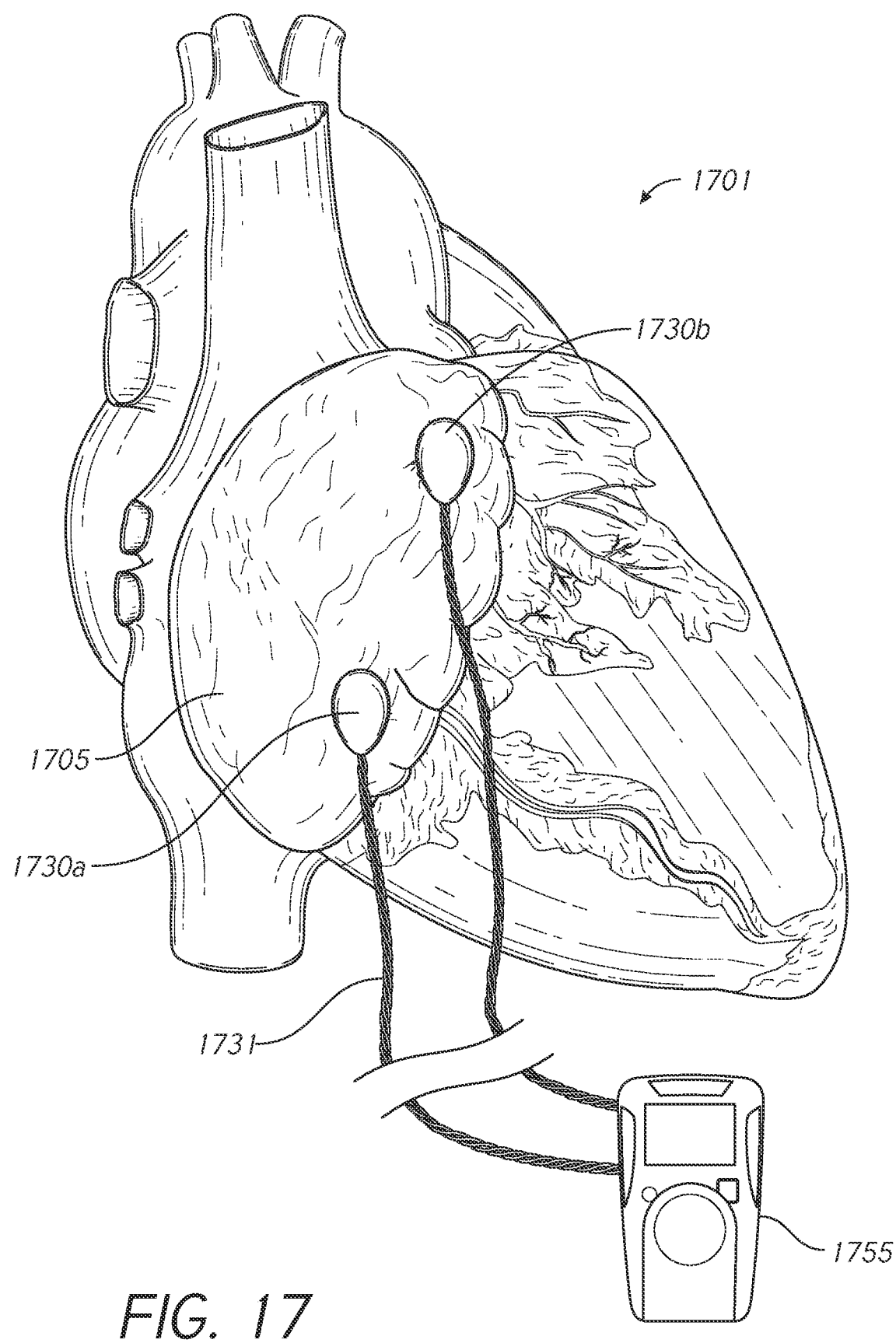
FIG. 17 illustrates a perspective view of a heart having one or more crystal devices implanted on an atrium thereof in accordance with one or more embodiments.

FIG. 17 illustrates a perspective view of a heart 1701 having one or more crystal devices 1730a, 1730b implanted on an atrium 1705 thereof in accordance with one or more embodiments. Although FIG. 17 shows a system for measuring stretch or modification in atrial issue, as with other embodiments disclosed herein, it should be understood that the principles disclosed herein apply to measurement of stretch or modification of other type of tissue or material. Crystal devices used in embodiments of the present disclosure may be at least partially coated with an epoxy 'lens' and disposed facing each other. In some embodiments, one or more components shown in FIG. 17 are configured such that an electrical signal is sent to one of the crystal devices 1730a, 1730b and is transformed into an audio signal that passes through the medium (e.g., air blood and/or biological tissue). The audio signal is received by the other crystal device, and is converted back into an electrical signal that is processed by the monitor device 1755. Generally, the distance between the crystal devices 1730a, 1730b may be derived or calculated by the monitor device 1755 from, or based at least in part on, the amount time elapsed between transmission from one crystal device and receipt of the signal by the other crystal device; that is, the time it takes the audio signal to pass between the crystal devices. The audio signal may advantageously comprise a signal in the frequency range of about 100 kHz to 100 MHz. Therefore, transmission of the signal may be effective in the natural media of the heart and/or chest cavity, which can include media comprising fluids and/or biological tissues (e.g., blood, muscle, fat, etc.). The presence of air in the chest cavity between the crystal devices may negatively impact the fidelity of the audio signal in some embodiments, but the signal power level and/or characteristics may be such as to nevertheless allow for satisfactory signal interpretation for distance determination. In some embodiments, actual distance is not calculated/determined, but rather in increase in a time parameter/value associated with signal propagation may indicate or allow for the determination of tissue stretch. Such determination may be independent of distance calculation/determination.

The crystal devices 1730a, 1730b are fixed or attached to the outside surface of the atrium 1705 (e.g., right atrium or left atrium) wall to detect stretching of the atrial tissue, such as for the purpose of atrial fibrillation prevention, as described in detail herein. The monitor device 1755 may be configured to measure the distance between the crystal device 1730a and the crystal device 1730b by performing a timing measurement of sound signals transmitted by one of the crystal devices and received by one or more crystal devices. Although two crystal devices are shown, it should be understood that any number of crystal devices may be used for tissue stretch/movement measurement in accordance with embodiments of the present disclosure. In some embodiments, the monitor 1755 and/or crystal devices 1730a, 1730b are configured to implement analog distance measurement, wherein the monitor 1755 is configured to integrate the time-of-propagation of audio signals between the crystal devices 1730a, 1730b as a voltage ramp function; the distance measurement may be based on the slope of the ramp and the electrical noise of system components. That is, length measurement may be related to and/or represented by an analog output voltage. In some embodiments, the monitor 1755 and/or crystal devices 1730a, 1730b are configured to implement digital distance measurement, wherein the time-of-propagation of audio signals between the crystal devices 1730a, 1730b is determined by incrementing high-speed digital counters; distance measurements may be output in the form of a digital number (e.g., the time-of-propagation count value). For example, when making measurements in biological cardiac tissue at body temperature, where the speed of propagation of sound waves may be approximately 1,590 m/s, a monitor operating with a clock speed of 128 MHz may have a spatial resolution of approximately 12 micrometers.

The crystal devices 1730a, 1730b may have any suitable or desirable size, and may advantageously be sized to be disposed in the relevant space and/or area of the outer surface of an atrium or other target tissue location. In some embodiments, the crystals 1730a, 1730b have a diameter of approximately 2 mm. The crystal devices 1730a, 1730b may be electrically coupled to the monitor 1755 in any desirable way. For example, the crystal devices 1730a, 1730b may be electrically coupled to the monitor 1755 by one or more conductors 1731, which may comprise copper wire, which may be suitable for short term chronic treatment (e.g., 1-4 weeks), and/or stainless-steel wire, which may be suitable for relatively longer-term chronic treatment (e.g., 1-6 months). In some embodiments, wire conductor(s) 1731 comprise insulator tubing, such as silastic tubing. The conductors 1731 may advantageously comprise a twisted pair of conductors corresponding to each crystal device.

Although the monitor device 1755 is illustrated as a singular device, it should be understood that the monitor 1755 functionality may be implemented by a plurality of discrete computing components or devices. The monitor device 1755 may be a relatively simple electronic device with alarm capabilities. For example, the monitor device 1755 may comprise or be coupled to one or more audio output devices, such as speaker(s), or the like, and/or one or more visual output devices, such as light sources(s) and/or display screen(s) for indicating that an alarm tissue stretch condition has been reached.

Figure 18:
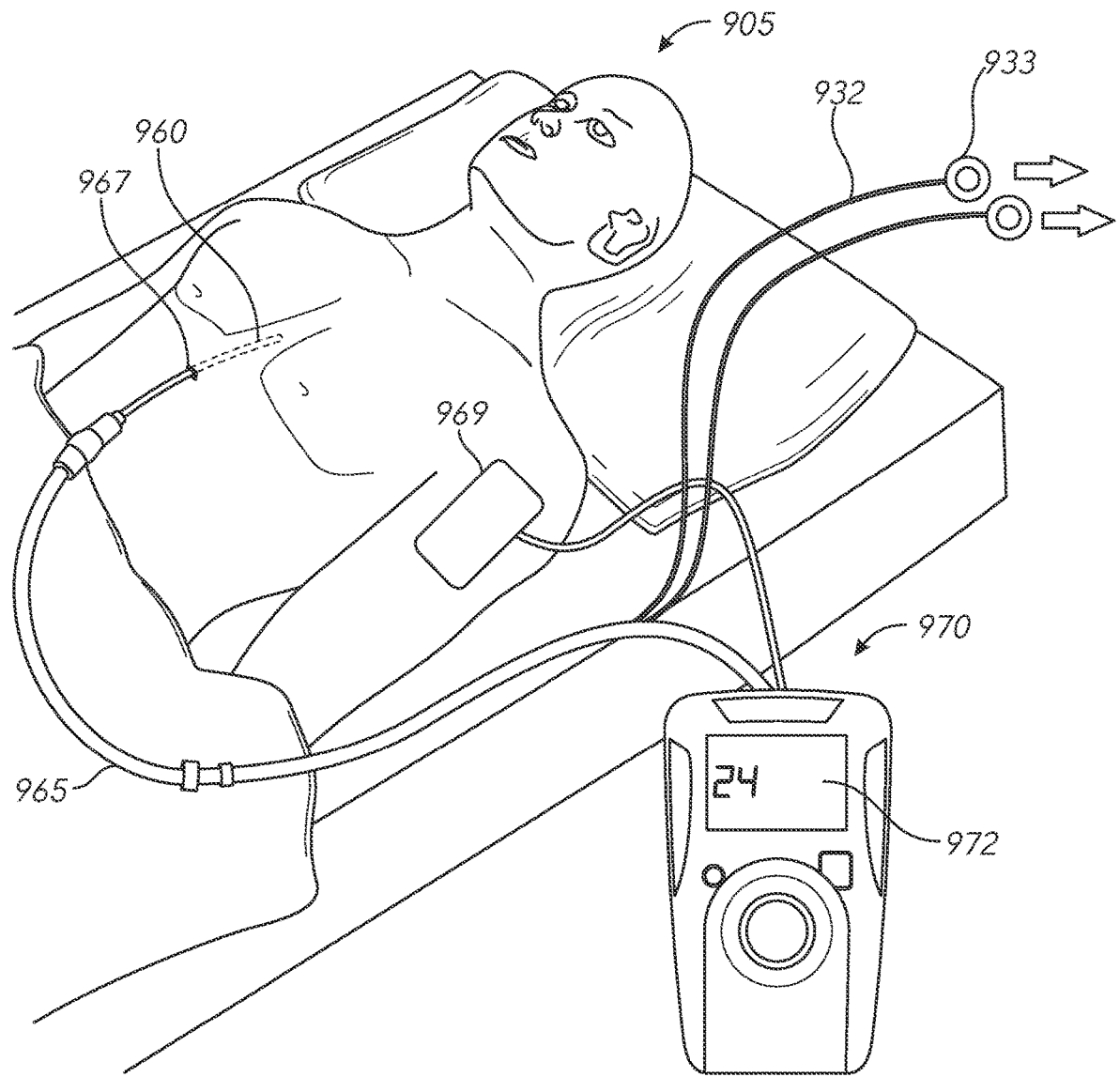
FIG. 18 illustrates an embodiment of a tissue stretch measurement system in accordance with one or more embodiments.

FIG. 18 illustrates an embodiment of a tissue stretch measurement system 900 in accordance with one or more embodiments. Implantation of the crystals 1730a, 1730b may be performed in any suitable or desirable way. For example, an implantation process may involve executing a stab wound with, for example, a 16-gauge needle to the desired/necessary depth in chest or abdomen of the patient. Using the supplied introducer the crystal is inserted into the hole. A purse string suture may be used to seal up the wound. Similarly to other embodiments disclosed herein, the system 900 of FIG. 18 includes a monitor device 970, which may be configured to provide stretch measurement functionality in combination with one or more implanted crystal devices, and may be embodied in one or more computing devices. The system 900 advantageously includes wired (or wireless) crystal devices (not shown) implanted in the chest cavity of the patient 905. The monitor 970 may be configured to supply electrical signals to one or more of the implanted crystal devices, which may be transmitted within the chest of the patient 905 as audio signals designed to propagate between two or more crystal devices. The crystal device(s) may be introduced to the target implantation site externally through a common access port 967, or separate crystal devices may be introduced through separate access ports, such as through a separate channel through the chest wall, or through a chest drainage tube, or the like. The monitor 970 may be configured to transmit electrical signals on one or more electrical conductors coupling the crystal device(s) to the monitor 970. Such signals may be powered by the monitor 970, which may receive power from an external source.

The monitor device may provide a stretch and/or distance determination functionality with respect to implanted crystal devices and may be configured tin alarm notification functionality. For example, the monitor 970 may receive return electrical signals from the implanted crystal device(s) and trigger an alarm or other notification or information display in response to the received signals. The monitor 970 may incorporate one or more light sources, which may be configured to provide an alarm or notification. Alternatively or additionally, the monitor 970 may comprise one or more other audio or visual components for providing alarm notifications. The monitor 970 may alarm or notify a physician or technician of early detection of atrial fibrillation, such that responsive or preventative measures may be implemented. The system 900 may further comprise an electrical ground structure or component 969, such as an adhesive ground pad or the like.

The monitor unit 970 may analyze the signals/waveforms from the crystal device(s) and identify changes in the signal/waveform. For example, the monitor 970 may be configured to identify a difference between a propagation time of an audio signal transmitted by a first crystal device and received at a second crystal device at a first time (e.g., associated with a calibration time) and a propagation time of an audio signal transmitted by the first crystal device and received at the second crystal device at a second time (e.g., after surgery). For example, during a period of time after surgery, an increase in propagation time of signals between a first crystal device and a second crystal device may indicate atrial stretch. Furthermore, if an electrical signal that is transmitted at a first crystal is not sensed at a second crystal, such condition may indicate a breakdown or disturbance in the electrical conduction path, which may be associated with atrial fibrillation.

The implanted crystal device(s) may be attached to the atrium surface using an attachment mechanism (e.g., suture or adhesive attachment) that is at least partially releasable by pulling a pull wire/string or engaging another release mechanism. For example, the diagram of FIG. 18 shows a plurality of pull wires 932, which may comprise any suture, string, line, wire, or other elongate attachment tool or material. In some embodiments, the pull wire 932 is coupled to a proximal manual engagement portion 933, such as a hoop, ring, trigger, hook, handle, or other structure or mechanism, wherein pulling on the engagement portion 933 in a proximal direction may cause an associated/attached crystal device or assembly to become at least partially detached from the tissue surface, allowing the crystal(s) to be removed from the patient (e.g., through the port 967. The releasability/removability of the crystal(s) may advantageously allow for the crystal(s) to be removed after surgery, thereby allowing for the use of crystals and/or materials that would be harmful or undesirable for permanent implantation.

The monitor 970 is configured to activate one or more alarm mechanisms in response to a determination of stretch beyond a pre-calibrated threshold. The stretch determination may be based on a distance calculation based on signals transmitted and/or received using the implanted crystal devices, or may be based on any other signal(s) or information provided by the crystal device(s). In some embodiments, a the relevant stretch threshold is associated with an increased distance between implanted crystal devices of approximately 5-10%, or greater, which may trigger alarm activation by the monitor 970.

Figure 19A:
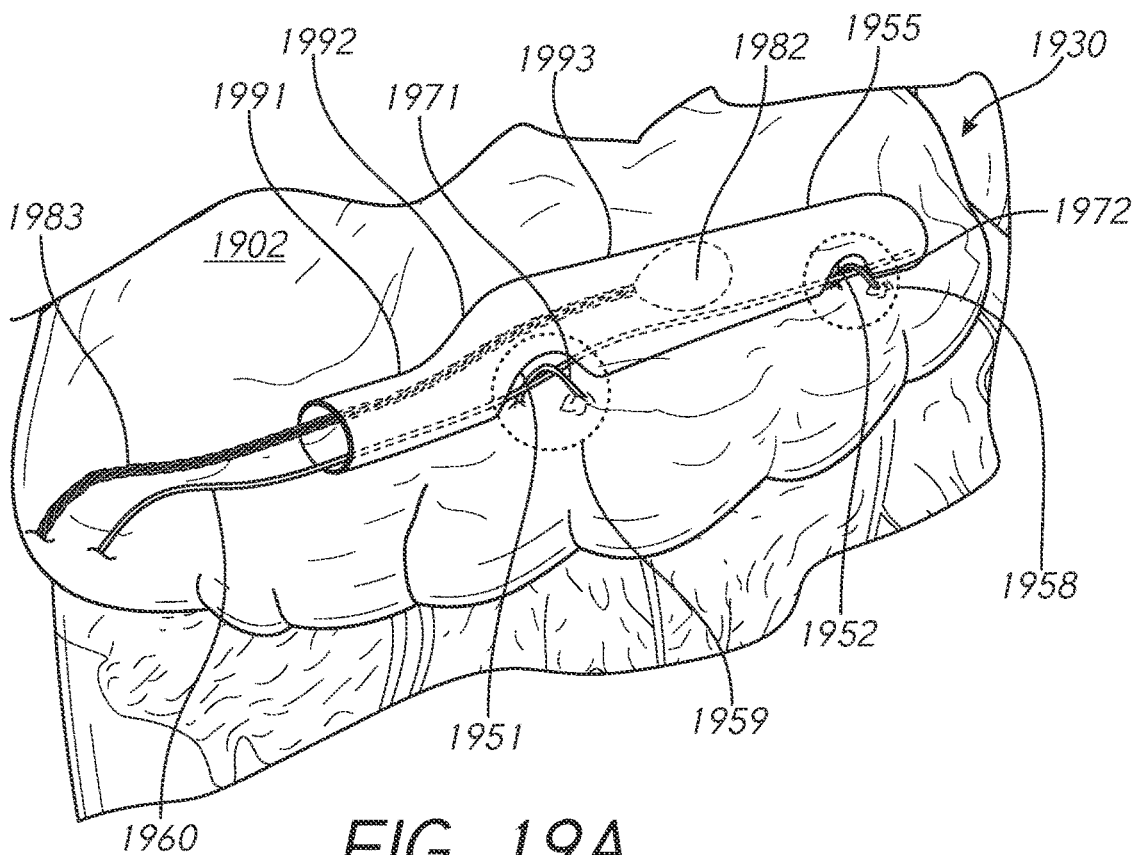
FIGS. 19A-19B illustrate aspects of a stretch-measurement crystal device in accordance with one or more embodiments.
Figure 19B:
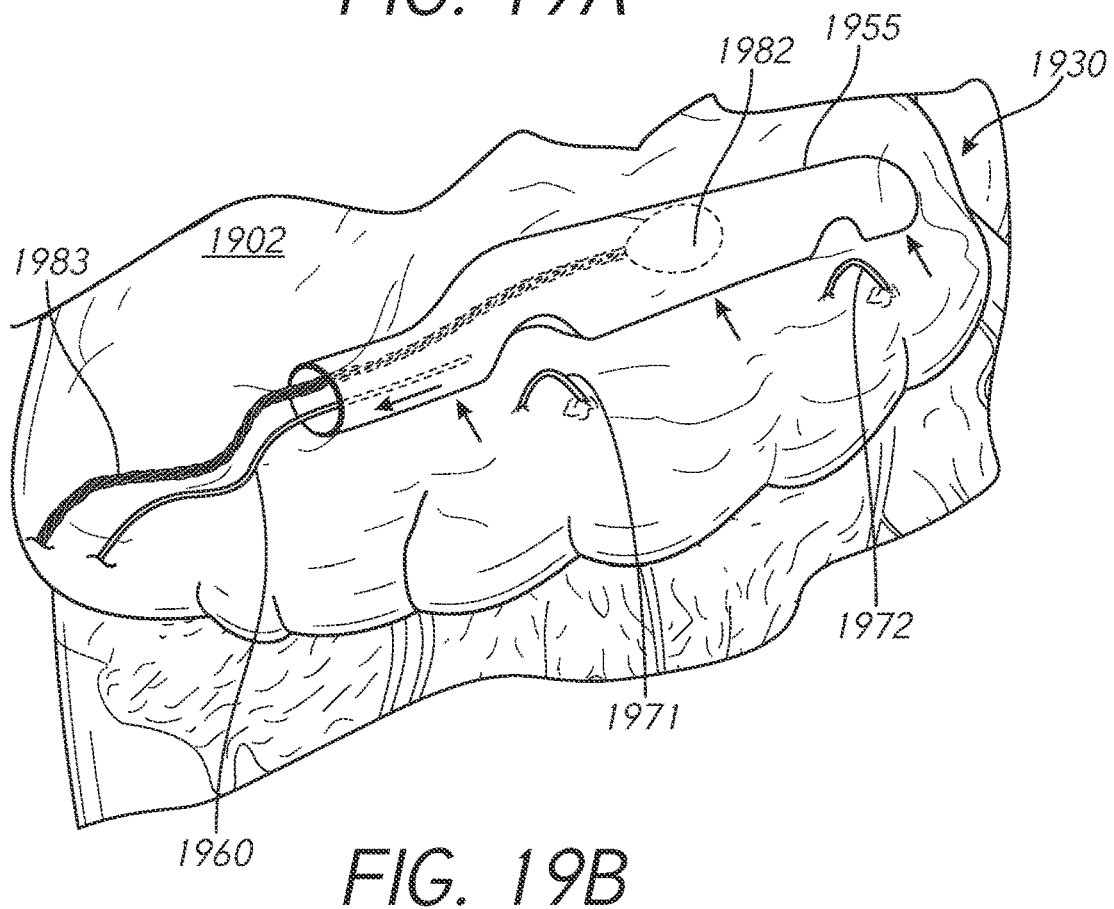

FIG. 19A-19B illustrate aspects of a stretch-measurement crystal device assembly in accordance with one or more embodiments. References herein to a "crystal device" may refer to a crystal and/or associated assembly or components/devices. The stretch-measurement crystal device 1930, and in particular the illustrated distal portion thereof, may be attached to, for example, the right atrium 1902 of a heart, such as on the anterior side of the right atrium, or on any other surface of tissue or other material. In some embodiments, the stretch-measurement crystal device 1930 may be attached to the left atrium (not shown), such as on a lateral side of the left atrium. FIG. 19 shows a close-up view, which may be similar in certain respects to the close-up views of the mechanical stretch-measurement probe 1250 shown in FIG. 12 and the electronic stretch-measurement probe 1650 shown in FIG. 16, described above. For example, the view of FIG. 19 illustrates a distal portion of the stretch-measurement crystal device 1930, which may be secured to one or more portions of the atrium surface.

The stretch-measurement crystal device 1930 includes an outer tube component 1955, which may house an inner crystal 1982 electrically coupled to one or more conductors 1983. In some embodiments, the conductor(s) 1983 comprise a twisted pair of conductors, as shown. The conductor(s) 1983 may allow for signals or waveforms received by the crystal(s) 1982 and/or transmitted by the crystal(s) 1982 to be generated and/or received/processed externally to the chest cavity of the patient. Such signals/waveforms may advantageously provide a relatively accurate measurement or indication of atrial stretch.

The device 1930 may be secured to the atrium surface at two points, such as at the illustrated regions 1959, 1958. Furthermore, the tube 1955 may incorporate a stretch expansion feature (not shown), which may be similar in certain respects to the stretch expansion feature 1656 of shown in FIG. 16 and described above; description of the expansion feature 1656 should be understood to apply to the tube 1955 of FIGS. 19A and 19B. Such stretch expansion features may advantageously allow for longitudinal expansion or stretching of the tube 1955 where the tube 1955 houses or is associated with multiple crystals, each of which are fixed to the tissue surface in some manner. In certain embodiments, the stretch-measurement crystal device 1930 may incorporate a pull-wire release feature to allow for removal of the device post-operatively, as described above in detail in connection with other mechanical and electrical stretch-measurement devices/probes.

The stretch-measurement crystal device 1930 may be operatively placed for measurement of atrial stretch, and may be attached to the atrium surface 1902 using one or more stitches (e.g., 1971, 1972). The audio signals received by one crystal from another crystal may be indicative of relative displacement of the crystals. The crystal 1982 may be housed in the tube 1955 or other housing, which may comprise plastic or other bio-compatible material. Although only one crystal 1982 and tube 1955 is shown, in some embodiments, two or more separate crystals and/or housings may be utilized, wherein a separate crystal and/or housing is associated with each of a plurality of tissue surface attachment points. In some embodiments, the tube housing 1955 includes a narrow portion 1991, a wider portion 1993, and a taper portion 1992 that is a transitional portion from narrow to wide. The wider portion 1993 may be sized/shaped to accommodate and/or hold the crystal(s) 1982. In some embodiments, the tube 1955 comprises multiple narrow, wide and transitional portions for holding/accommodating a plurality of crystals. Although two sutures are shown in FIGS. 19A and 19B, in some embodiments, only one suture, or more than two sutures, attaches the tube 1955 or associated components to the surface 1902.

In some embodiments, the attachment suture(s) (e.g., 1971, 1972) can remain attached to the tissue surface indefinitely or permanently, while the remaining components of the assembly 1930 may be removed. Where two crystals are housed in the same housing, it may be necessary for the housing to not significantly restrain movement, and therefore such embodiments may advantageously employ a helically-cut tube configuration as described above with respect to other embodiment. In some embodiments, crystals can be individually attached to the atrial wall, or multiple crystals can be attached to a strain device, as was described in connection with one or more other embodiments.

In some embodiments, the crystal 1982 is not fixed to the tube 1955, but rather, the tube 1955 is fixed to the tissue surface via a suture 1972 and a pull wire 1960, which may be disposed at least partially within the tube 1955 and engaged by the suture 1952 through an aperture or gap 1952. Removal of the stretch-measurement crystal device 1930 may be achieved in a manner similar to those described above in connection with mechanical and electrical stretch-measurement probes. For example, the stretch-measurement crystal device 1930 may be withdrawn, such as after implementation of a wire or other detachment mechanism, through a chest tube or other chest or torso access conduit/channel.

The stretch-measurement crystal device 1930 may advantageously allow for desirable resolution with respect to stretch-measurement readings. Furthermore, the electrical readings generated by the stretch-measurement crystal device 1930 may allow for noise associated with pumping of the chambers of the heart and/or pacing of the heart to be filtered out, thereby providing improved measurement of atrial stretch. For example, the crystal(s), while implanted, may generate data indicating tissue movement associated with heartrate and/or other atrial tissue displacement. In some implementations, a mean value of displacement of the crystals may be used to determine atrial stretch. Furthermore, one or more frequency-domain filters may be used to filter out signal components associated with the cardiac cycle frequency. The crystal(s) 1982 may generally be insulated, such as encapsulated or enclosed in polymer or other protective material. Furthermore, the conductor(s) 1983 running to the crystal(s) 1982 may be encapsulated in insulating material.

FIG. 19B shows a detachment stage of the stretch-measurement crystal device 1930 according to one or more embodiments. As described above, the crystal device 1930 can be placed/attached onto the atrial wall and can be removed at or near the time of patient discharge in a similar manner as temporary pacing leads. The pull wire 1960 may be pulled to detach the device 1930 from the atrial wall and may secure the device 1930 to the atrial wall via one or more sutures. For example, the two illustrated sutures 1971, 1972 can be placed into the atrial wall to fix the location of the crystal 1982, which may be fixed to the tube 1955 or otherwise maintained in the desired position within the tube. Once the pull wire is removed, the crystal sensor device 1930 may no longer be fixed to the atrial wall, such that it may be freely removed. Although FIGS. 19A and 19B show a tube housing 1955, in some embodiments, the crystal(s) 1982 may be directly attached to the tissue wall without a housing associated therewith. Although illustrated as sutures 1971, 1972, such features may comprise any suitable or desirable means for affixing a device to tissue known by those having ordinary skill in the art and/or described or referenced herein. The removability feature(s) of the measurement device 1930 advantageously provide a convenient mechanism for measuring tissue stretching, while not requiring permanent implants or prolonged maintenance of implanted device(s) in the body, which can improve long-term health prospects compared to permanent or long-term implant devices.

Depending on the embodiment, certain acts, events, or functions of any of the processes described herein can be performed in a different sequence, may be added, merged, or left out altogether. Thus, in certain embodiments, not all described acts or events are necessary for the practice of the processes. Moreover, in certain embodiments, acts or events may be performed concurrently.

Depending on the embodiment, certain acts, events, or functions of any of the processes described herein can be performed in a different sequence, may be added, merged, or left out altogether. Thus, in certain embodiments, not all described acts or events are necessary for the practice of the processes. Moreover, in certain embodiments, acts or events may be performed concurrently.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A method of monitoring stretch in an organ, the method comprising:

attaching a first magnet to an exterior surface of a right atrium of a heart of a patient at a first position;
attaching, separately from the first magnet, a second magnet to the exterior surface of the right atrium at a second position, the second position being spaced from the first position by a first distance;
introducing an intravenous bolus of saline fluid into a blood vessel of the patient;
using an array of Hall Effect sensors of a monitor device, through a closed chest wall of the patient:
sensing a post-bolus position of the first magnet; and
sensing a post-bolus position of the second magnet;
determining a post-bolus distance between the first magnet and the second magnet caused by stretching of the atrium in response to the intravenous bolus of saline fluid, the post-bolus distance being greater than the first distance;
calibrating an alarm setpoint based on the post-bolus distance;
using the array of Hall Effect sensors of the monitor device, through the closed chest wall of the patient:
sensing a third position of the first magnet; and
sensing a fourth position of the second magnet;
determining a second distance between the first magnet and the second magnet based on the third position and the fourth position; and
triggering an alarm based on a determination that the second distance is greater than the post-bolus distance.

2. The method of claim 1, further comprising:
determining a baseline blood pressure prior to introducing the intravenous bolus of saline fluid distance between the first magnet and the second magnet; and
determining a post-bolus blood pressure after introducing the intravenous bolus of saline fluid;
wherein said calibrating the alarm setpoint is based on at least one of the baseline blood pressure or the post-bolus blood pressure.

3. The method of claim 1, wherein:
said attaching the first magnet and the second magnet to the exterior surface of the right atrium is performed through an open-chest access to the heart; and
said determining the second distance is performed post operatively when a chest of the patient is closed.

4. The method of claim 1, wherein said determining the second distance between the first magnet and the second magnet is performed external to a body of the patient.

5. The method of claim 1, wherein the intravenous bolus of saline fluid comprises at least 100 mL of saline fluid.

6. The method of claim 1, further comprising interrogating a radio-frequency identification (RFID) tag associated with at least one of the first magnet or the second magnet.

7. The method of claim 1, wherein:
the monitor device is secured to a chest of the patient using at least one of an adhesive pad or a strap;
each of the array of Hall Effect sensors is associated with one of a plurality of light sources, the plurality of light sources having a brightness characteristic that is based on a proximity of a respective Hall Effect sensor to one of the first magnet or the second magnet; and
output of ones of the plurality of light sources provides a visual indication of positions of the first and second magnets.

8. The method of claim 1, wherein the monitor device comprises a display configured to display a representation indicating an actual physical position behind the monitor device of at least one of the first magnet or the second magnet.

9. The method of claim 1, further comprising attaching a third magnet to the exterior surface of the right atrium of the heart, wherein said triggering the alarm is further based on a determination that the third magnet has increased in separation distance from the first magnet.

10. A method of monitoring stretch in an organ, the method comprising:
   accessing a heart of a patient;
   implanting a first sensor device including a first inductive coil on a surface of an atrium of the heart;
   implanting a second sensor device including a second inductive coil on the surface of the atrium;
   introducing an intravenous bolus of saline fluid into a blood vessel of the patient;
   using a monitor device, through a closed chest wall of the patient:
      inductively sensing a post-bolus position of the first sensor device; and
      inductively sensing a post-bolus position of the second sensor device;
   determining a post-bolus distance between the first sensor device and the second sensor device caused by stretching of the atrium in response to the bolus of saline fluid based on the post-bolus position of the first sensor device and the post-bolus position of the second sensor device;
   using the monitor device, through the closed chest wall:
      inductively sensing a first position of the first sensor device; and
      inductively sensing a second position of the second sensor device;
   determining a first distance between the first position and the second position; and
   providing an alarm output in response to a determination that the first distance exceeds the post-bolus distance.

11. The method of claim 10, further comprising:
   suturing the first sensor device to the surface of the atrium through an aperture of the first sensor device; and
   suturing the second sensor device to the surface of the atrium through an aperture of the second sensor device.

12. The method of claim 10, wherein the alarm output comprises at least one of blinking light output or audible alarm output.

13. The method of claim 10, further comprising wirelessly powering the first and second sensor devices using an inductive coil of the monitor device.

14. The method of claim 10, further comprising:
   determining a second distance between the first sensor device and a third sensor device implanted on the surface of the atrium; and
   determining a third distance between the second sensor device and the third sensor device.

15. The method of claim 14, wherein the first sensor device, the second sensor device, and the third sensor device are arranged in a triangular arrangement on the surface of the atrium.

16. The method of claim 10, wherein the first sensor device comprises a magnet.

* * * * *